US012485232B2

(12) United States Patent
Love et al.

(10) Patent No.: US 12,485,232 B2
(45) Date of Patent: *Dec. 2, 2025

(54) PRE-FILLED SYRINGE SAFETY DEVICES AND INJECTORS, SYSTEMS, AND METHODS OF USE

(71) Applicant: Love Lifesciences LLC, Olathe, KS (US)

(72) Inventors: Nicholas Love, Olathe, KS (US); Bradley Hopper, Topeka, KS (US)

(73) Assignee: Love Lifesciences LLC

( * ) Notice: Subject to any disclaimer, the term of this patent is extended or adjusted under 35 U.S.C. 154(b) by 0 days.

This patent is subject to a terminal disclaimer.

(21) Appl. No.: 19/004,370

(22) Filed: Dec. 29, 2024

(65) Prior Publication Data

US 2025/0135124 A1 May 1, 2025

Related U.S. Application Data

(63) Continuation of application No. 18/285,671, filed as application No. PCT/US2022/023878 on Apr. 7, 2022, now Pat. No. 12,214,180.

(60) Provisional application No. 63/172,512, filed on Apr. 8, 2021.

(51) Int. Cl.
*A61M 5/32* (2006.01)
*A61M 5/315* (2006.01)

(52) U.S. Cl.
CPC ........ *A61M 5/3245* (2013.01); *A61M 5/3158* (2013.01); *A61M 5/3213* (2013.01); *A61M 5/3271* (2013.01); *A61M 2005/3247* (2013.01)

(58) Field of Classification Search
CPC .............. A61M 5/3245; A61M 5/3158; A61M 5/3213; A61M 5/3271; A61M 2005/3247; A61M 5/3137; A61M 5/31581; A61M 5/31586; A61M 5/31576; A61M 5/31578; A61M 5/31583; A61M 5/3243; A61M 5/326; A61M 5/3272; A61M 5/3202; A61M 5/3204; A61M 2005/3139; A61M 2005/3204; A61M 2005/3213
See application file for complete search history.

(56) References Cited

U.S. PATENT DOCUMENTS

| | | | | |
|---|---|---|---|---|
| 4,988,339 | A | 1/1991 | Vadher | |
| 9,233,213 | B2 * | 1/2016 | Olson ................. | A61M 5/3213 |
| 2005/0222539 | A1 | 10/2005 | Gonzales et al. | |

(Continued)

*Primary Examiner* — Kevin C Sirmons
*Assistant Examiner* — Leah J Swanson
(74) *Attorney, Agent, or Firm* — Polsinelli PC

(57) ABSTRACT

A prefilled syringe safety device and injector for use with a syringe. The prefilled syringe safety device and injector includes a cartridge, a casing, a tube, a biasing member, a ring and a plunger slider. The cartridge supports the syringe therein. The cartridge is supported within the casing. The tube includes a tube distal end. The tube is slidably engaged with the cartridge and can be in an extended state and in a retracted state. When in the retracted state, the needle of the syringe extends beyond the tube distal end and the casing distal opening. The biasing member is engaged with the cartridge and the tube to bias the tube in the extended state. The ring includes a protrusion and is engaged with the tube and the biasing member. The protrusion is positioned within the track. The plunger slider engages with the plunger of the syringe.

24 Claims, 29 Drawing Sheets

(56) References Cited

U.S. PATENT DOCUMENTS

| | | | | |
|---|---|---|---|---|
| 2011/0311833 | A1 | 12/2011 | Parker et al. | |
| 2020/0353170 | A1* | 11/2020 | Atterbury | A61M 5/2033 |
| 2021/0093797 | A1* | 4/2021 | Finkelstein | A61M 5/2033 |
| 2024/0082506 | A1* | 3/2024 | Love | A61M 5/3158 |

* cited by examiner

PRE-FILLED SYRINGE SAFETY DEVICES AND INJECTORS, SYSTEMS, AND METHODS OF USE

CROSS-REFERENCE TO RELATED APPLICATION

This application is a continuation of U.S. application Ser. No. 18/285,671, filed Oct. 5, 2023, which application is a national stage entry of PCT Application No. PCT/US2022/023878, filed Apr. 7, 2022, which PCT application claims the benefit of U.S. Provisional Application No. 63/172,512, filed Apr. 8, 2021. All the afore-mentioned applications are hereby incorporated by reference in their entireties into the present application for all purposes.

TECHNICAL FIELD

The present disclosure relates to a pre-filled syringe safety devices and injectors, systems, and methods of use. More particularly, the disclosure relates to pre-filled syringe safety devices and injectors, systems, and methods that are manually actuated to deliver a dose of a drug.

BACKGROUND

Auto-injectors are medical devices that deliver a single dose of a drug via an enclosed, spring-loaded syringe. Conventionally, auto-injectors are designed to be self-administered, but can be administered by others. Auto-injectors are relatively easy to administer as compared with a syringe and needle, which require dosing of the drug into the syringe. Auto-injectors can mitigate fears associated with seeing an exposed needle. But, some patients may also fear the abrupt stab of the needle from auto-injectors.

Despite auto-injectors and conventional syringes and needles, many patients still fear needle injections. The fear can be so great that some patients may even quit administering their medications due to problems they face with auto-injectors and other injection methods. This causes problems for physicians looking to maintain patients on injectable therapies, insurance companies covering patients requiring injectable therapies, and pharmaceutical companies looking to maintain patients on their medications.

It is with these thoughts in mind, among others, that aspects of the pre-filled syringe safety devices and injectors were conceived. By utilizing the pre-filled syringe safety devices and injectors described herein, patients will be more likely to maintain use of their medications as there will be less reasoning to stop taking their medications. Increased medication maintenance provides improved health outcomes for patients and improved experiences for all entities involved in the injection market.

SUMMARY

Aspects of the present disclosure includes an injector for use with a syringe having a plunger, a barrel, and a needle. The injector may include a cartridge, a casing, a tube, a biasing member, a ring, and a plunger slider. The cartridge may be configured to support the syringe therein. The casing includes a tubular body, a casing distal opening, an inner surface, an internal volume, a slider slot extending through the tubular body, and a track defined on the inner surface. The cartridge is supported within the casing. The tube includes a tube distal end, the tube slidably engaged with the cartridge and may be configured to be in an extended state and in a retracted state, wherein, in the retracted state, the needle of the syringe extends beyond the tube distal end and the casing distal opening. The biasing member may be engaged with the cartridge and the tube so as to bias the tube in the extended state. The ring may include a protrusion and be engaged with the tube and the biasing member. The protrusion may be positioned at least partially within the track. The plunger slider may have a first portion configured to engage with the plunger of the syringe within the internal volume of the casing. The plunger slider may have a second portion extending from the first portion and may be configured to be guided by the slider slot to depress the plunger of the syringe.

In certain instance, in the extended state, the tube extends distally past a tip of the needle.

In certain instance, the injector further may include a distal cap may be configured to couple to the tube distal end of the tube.

In certain instance, the distal cap includes a tubular extension having an opening sized to receive and secure a needle cap of the syringe therein such that removal of the distal cap from the tube distal end of the tube also removes the needle cap from the syringe.

In certain instance, the tube is may be configured to transition from the extended state, to the retracted state, and then to a locked extended state via interaction of the protrusion of the ring with the track.

In certain instance, the tube further includes a plurality of nubs at the distal tube end.

In certain instance, the casing further includes a longitudinal axis, the slider slot including a first section that is transverse to the longitudinal axis and a second section that is parallel to the longitudinal axis.

In certain instance, the casing further includes at least one viewing window extending through the tubular body.

In certain instance, the injector further may include the syringe being pre-filled with a dose of a substance.

In certain instance, the inner surface of the casing includes recess may be configured to receive and secure a flange of the syringe therein.

Aspects of the present disclosure may include an injector for use with a syringe having a plunger, a barrel having a flange, and a needle. The injector may include cartridge, a casing, a tube, and a plunger slider. The cartridge may be configured to support the syringe therein. The casing may include a body, a casing distal opening, an internal volume, and a slider slot extending through the body, the cartridge supported within the casing. The tube may include a tube distal end, the tube slidably engaged with the cartridge and biased so the tube distal end extends distally past a tip of the needle and distally past the casing distal opening, the tube may be configured to retract proximally upon overcoming a biasing force such that the needle of the syringe extends beyond the tube distal end and the casing distal opening. The plunger slider has a first portion that may be configured to engage with the plunger of the syringe within the internal volume of the casing, the plunger slider having a second portion extending from the first portion and may be configured to be along the slider slot to depress the plunger of the syringe.

In certain instance, the injector further may include the pre-filled syringe filled with a dose of a drug.

In certain instance, the outer tube further includes a channel guide defined on the inner surface of the outer tube, and the plunger slider further includes a protrusion, the protrusion may be configured to slide within the channel guide as the plunger slider guides depression of the plunger.

In certain instance, the casing includes a recess may be configured to support the flange of the barrel of the syringe.

In certain instance, the casing includes at least one window defined therein may be configured to provide a view of the barrel of the syringe.

In certain instance, the tube is in sliding relation to the cartridge, and wherein a biasing member is operably coupled between the tube and the cartridge.

In certain instance, the casing includes a track defined on an inner surface thereof, wherein the tube is in engagement with the track and the tube is may be configured to lock in an extended state.

In certain instance, the tube is may be configured to lock in an extended state only after the tube has been retracted relative to the casing.

In certain instance, the injector further may include a spring may be configured to provide the biasing force.

In certain instance, the spring provides a rotational bias to a lock ring coupled to the tube, the rotational bias may be configured to lock the tube in an extended state.

Aspects of the present disclosure may include a method of injecting a substance into an injection site of a patient. The method may include positioning a distal tube of an injector adjacent the injection site of the patient, the injection may include: a casing having an opening at a distal end thereof; a cartridge housed within the casing and supporting a syringe therein, the syringe enclosing the substance therein and including a barrel, a needle, and a plunger; a plunger slider engaged with the plunger of the syringe; the distal tube being slidingly coupled with the cartridge and biased into an extended position such that the distal tube extends over the needle and at least partially outwards from the opening at the distal end of the casing. The method may include depressing the distal tube against the injection site of the patient thereby causing the distal tube to be in a retracted position wherein the needle protrudes past the distal tube and into the injection site of the patient. The method may include distally advancing the plunger slider relative to the casing so as to depress the plunger within the barrel of the syringe to dispense the substance from the barrel, through the needle, and into the injection site of the patient. And, the method may include retracting the distal tube from the injection site of the patient thereby causing the distal tube to lock in the extended position.

In certain instance, the method further may include rotating the plunger slider relative to the casing prior to distally advancing the plunger slider relative to the casing.

In certain instance, distally advancing the plunger relative to the casing is restricted until the plunger slider is rotated.

In certain instance, the injector further includes a lock ring coupled to the distal tube, the lock ring including a feature that is guided by a corresponding feature on the casing to facilitate the distal tube being locked in the extended position.

In certain instance, the feature is a post, and the corresponding feature is a track formed on an inner side of the casing.

Aspects of the present disclosure can include an injector for use with a syringe having a plunger, a barrel, and a needle. In certain instances, the injector may include a cartridge, a casing, a tube, a biasing member, a ring and a plunger slider. The cartridge can support the syringe at least partially therein. The casing can include first and second openings, an inner surface, an outer surface opposite the inner surface, and a track defined on the inner surface. The casing can support the cartridge and the syringe. The tube can include a tube distal end. The tube can be slidably engaged with the cartridge and configured to extend and retract relative to the first opening of the casing. And, in a retracted state of the tube and with the casing supporting the cartridge and the syringe, the needle of the syringe can extend beyond the tube distal end and the first opening of the casing. The biasing member can be engaged with the cartridge and the tube so as to bias the tube in an extended state of the tube. The ring can include a protrusion and be engaged with the tube and the biasing member. The protrusion can be positioned at least partially within the track. The plunger slider can couple to the plunger of the syringe and be positioned at least partially outside the casing. When the plunger slider and the plunger of the syringe are coupled together, movement of the plunger slider and the plunger are fixed.

In certain instances, the cartridge and the casing are removably coupled together. In certain instances, the plunger slider extends at least partially through the second opening. In certain instances, the second opening extends through a sidewall of the casing. In certain instances, the second opening includes a linear section. In certain instances, the second opening includes a transverse section proximal to the linear section.

In certain instances, the inner surface defines an internal volume, and the plunger slider is configured to engage with the plunger of the syringe within the internal volume of the casing.

In certain instances, the protrusion of the ring is positioned at least partially within the track and is configured to lock the tube in the extended position after the tube has been in the retracted state.

In certain instances, the ring is configured to rotate relative to the tube at least partially when the ring is engaged with the tube and the biasing member.

In certain instances, the casing is configured to support the cartridge and the syringe in a fixed position relative to the casing during movement of the plunger slider.

In certain instances, the barrel of the syringe includes a flange, and the inner surface of the casing includes a structure configured to contact the flange of the barrel of the syringe in order to facilitate the fixed position of the syringe relative to the casing during movement of the plunger slider.

In certain instances, movement of the plunger slider is independent of movement of the tube. In certain instances, rotation of the plunger slider is inhibited once the plunger slider is moved distally.

In certain instances, the injector further comprising the syringe. In certain instances, the injector comprising a medicament housed within the syringe. In certain instances, the injector comprising a cap configured to releasably couple to an end of the casing.

In certain instances, the inner surface defines an internal volume, and the plunger of the syringe is positioned entirely within the internal volume of the casing.

In certain instances, the plunger slider comprises a proximal-facing engagement surface for use in at least assisting to moving the plunger slider distally. In certain instances, the plunger slider further comprises a side-facing engagement surface for use in at least assisting to moving the plunger slider distally.

In certain instances, a rate of movement of the plunger slider is manually controlled.

Aspects of the present disclosure can include a method of employing the injector having the casing supporting the cartridge and the syringe. The method may include applying the tube to an injection site thereby causing the tube to be in the retracted state thereby causing the needle to enter the injection site. The method may further include depressing the plunger slider at a user-controlled rate thereby causing dispensing of at least some of the medicament from the syringe into the injection site. The method may further include removing the tube from the injection site thereby causing the tube to be locked in the extended state shielding the needle.

In certain instances, depressing of the plunger slider is independent of applying the tube to the injection site. In certain instances, depressing the plunger slider is performed at a user-controlled amount in order to dispense all of the medicament. In certain instances, depressing the plunger slider is performed at a user-controlled amount in order to dispense less than all of the medicament.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. It should be noted that the drawings are not necessarily to scale; however the emphasis instead is being placed on illustrating the principles of the inventive concepts. Also, in the drawings the like reference characters may refer to the same parts or similar throughout the different views. It is intended that the embodiments and figures disclosed herein are to be considered illustrative rather than limiting.

DETAILED DESCRIPTION

Figure 1A:
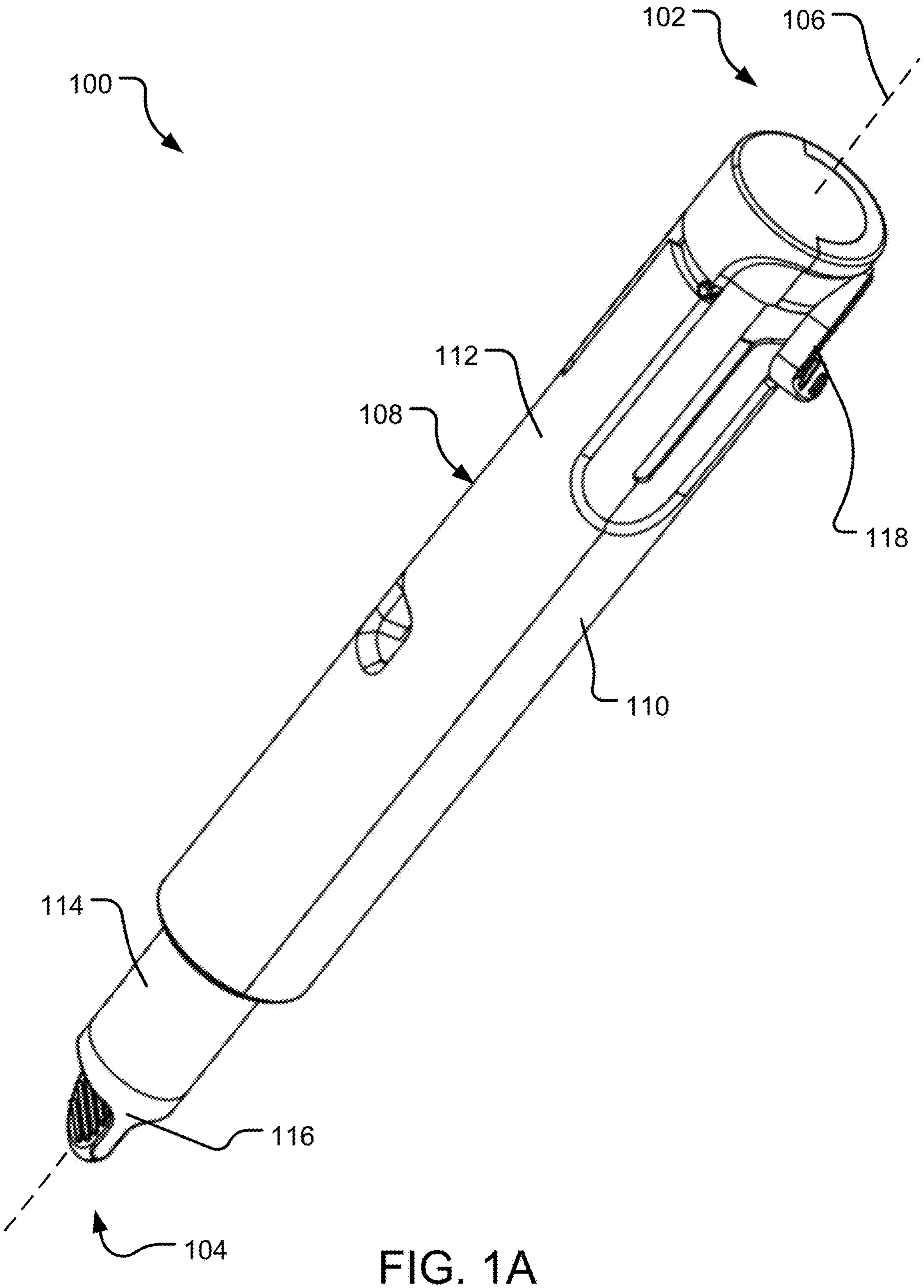
FIG. 1A is an isometric view of a pre-filled syringe safety device and injector (referred to as "an injector" hereinafter) in an assembled state.
Figures 1B, 1C, 1D, 1E:
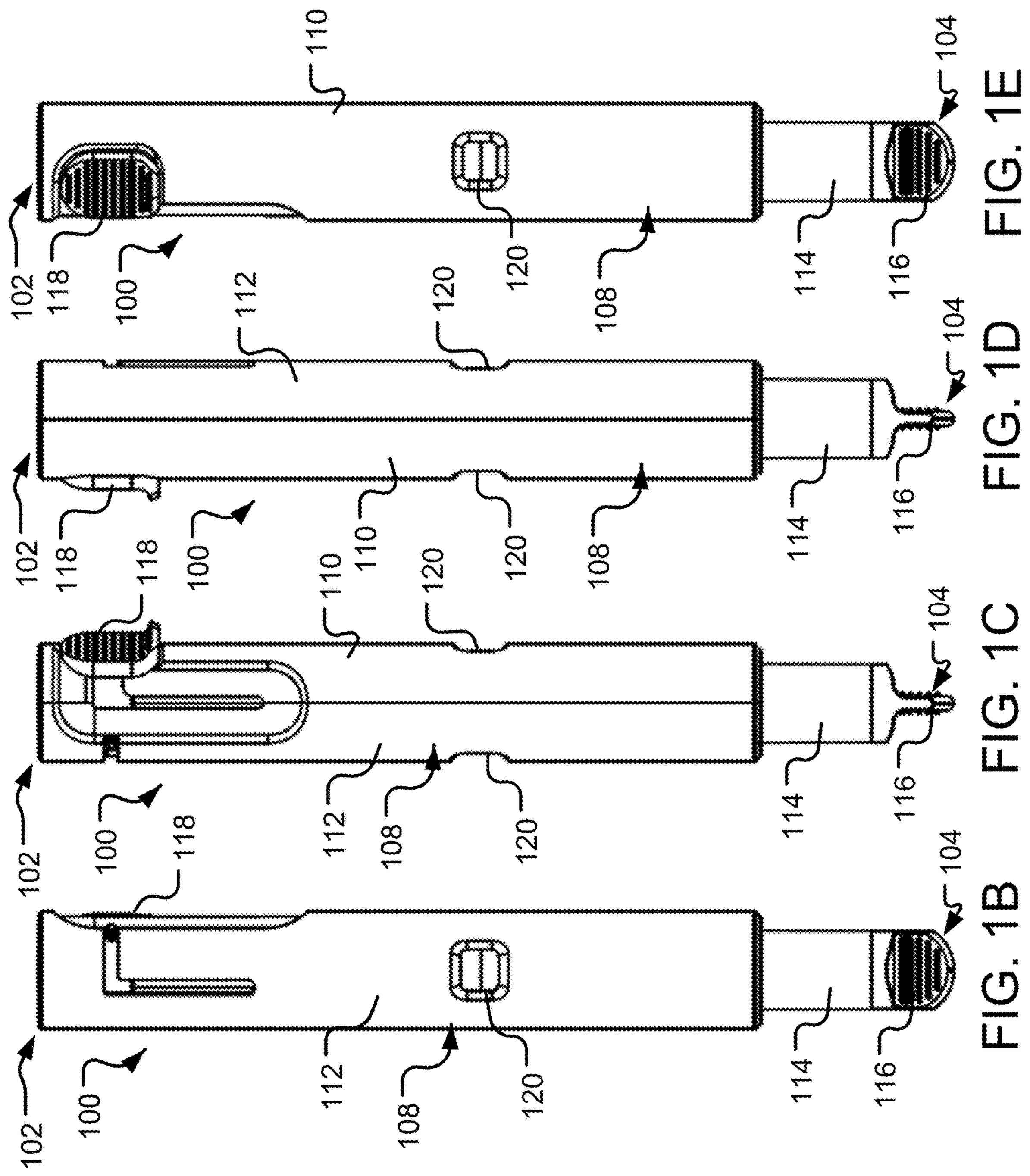
FIGS. 1B-1E are, respectively, side views of the injector in an assembled state in four different rotational orientations.

FIG. 1A is an isometric view of a pre-filled syringe safety device and injector 100 (referred to as "an injector" or "the device" hereinafter) in an assembled state. The injector 100, as referred to herein, may include a pre-filled syringe that includes a dose of a substance (e.g., drug). Alternatively, the injector 100 may be without a pre-filled syringe. The injector 100 may be one component of an injector system that includes a pre-filled syringe. The injector 100 may be one component of a kit that includes the pre-filled syringe, packaging, and instructions for use.

The injector 100 as described herein allows for a pre-filled syringe to be loaded into the device for injection of a dose of a substance. The injector described and shown herein permits a user to inject the needle into an injection site at his or her own pace, and then manually inject the medication. This is different than conventional auto-injectors, which inject and dispense medication in a single step. With the injector 100 described herein, the needle may be shielded by a portion the device before and after use. And after use, the needle may be locked from further exposure outside of the device. Thus, injection of the substance is performed manually by the user after the needle is exposed (and injected) into an injection site. The device may also inhibits dispensing of the substance from the pre-filled syringe until the needle is exposed.

The pre-filled syringe includes a barrel holding a substance (e.g., drug), a plunger slidingly engaged with the barrel, and a needle coupled to the barrel opposite the plunger. The barrel may also include a flange or projection at a proximal end thereof.

Referring to FIG. 1A, the injector 100 includes a proximal end 102, a distal end 104 opposite the proximal end 102, and a longitudinal axis 106 extending longitudinally through the proximal and distal ends 102, 104. The injector 100 includes a casing 108, which includes first and second casings 110, 112, respectively, that are designed to be affixed to each other via snaps, clips, or the like. The casing 108 of the injector 100 is not limited to a two-part casing. In certain instances, the casing 108 may be a single piece. In certain instances, the casing 108 may be more than two pieces. Still referring to FIG. 1A, the injector 100 further includes a tube 114 at the distal end 104. The tube 114 is moveable relative to the casing 108. More particularly, the tube 114 is biased in the extended position shown in FIGS. 1A and 1*s* retractable relative to the casing 108 upon the application of a force to the tube 114 that overcomes the biasing.

The injector 100 further includes a cap 116 that is coupled to the tube 114. The cap 116 may be sized to also couple to a needle cap of the syringe (not shown) that covers the needle. Conventionally, pre-filled syringes are manufactured with a needle cap in place to guard the needle. In this way, the injector 100 can be assembled into an injector system in a sterile environment with the needle cap in place and with the cap 116 sized to couple to the needle cap. Then, upon removal of the cap 116 from the tube 114, the cap 116 also removes the needle cap.

The injector 100 further includes a plunger slider 118 near the proximal end 102 thereof. The plunger slider 118 is engaged with the plunger of the syringe, which is housed or enclosed within the injector 100. As will be described in this application in reference to subsequent figures, the plunger slider 118 is rotatable transversely to the longitudinal axis 106 and, then, it is distally depressible so as to dispense the substances within the syringe.

FIGS. 1B-1E are, respectively, side views of the injector 100 in an assembled state in four different rotational orientations. As seen in the figures, a window 120 is defined in each of the casings 110, 112. The window 120 is a passageway through the casings 110, 112 so the syringe and/or the substance within the barrel of the syringe is visible. Thus, a user can visually see if the injector 100 is loaded with a pre-filled syringe.

Figure 1F:
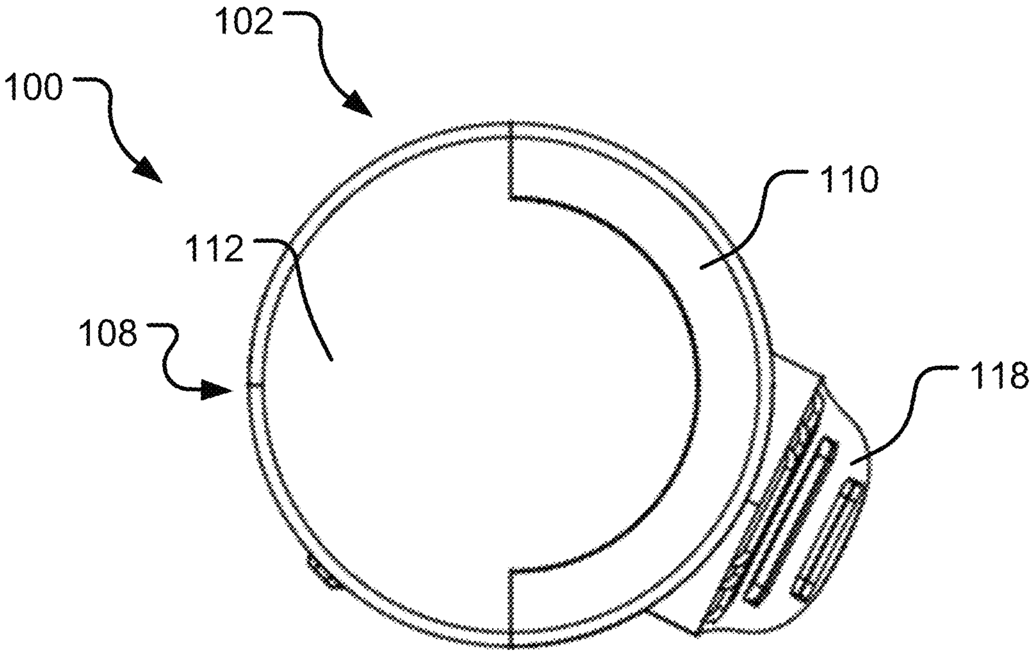
FIGS. 1F and 1G are, respectively, top and bottom views of the injector in an assembled state.
Figure 1G:
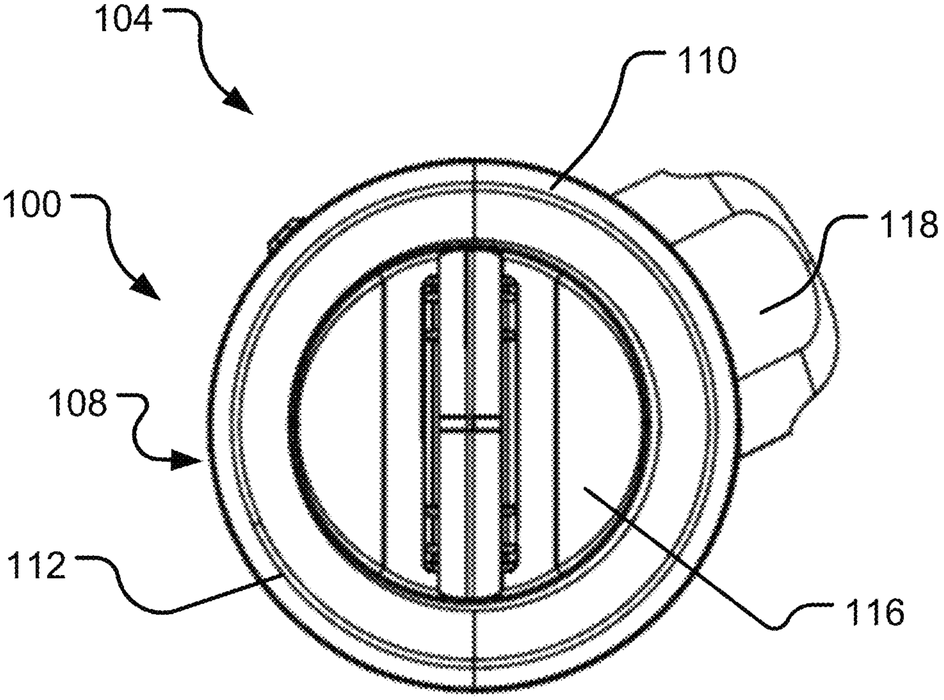

FIGS. 1F and 1G are, respectively, top and bottom views of the injector 100 in the assembled state. The casing 108 defines a generally circular perimeter with the plunger slider 118 jutting out from the perimeter. In this way, a user can easily and conveniently rotate and depress the plunger slider 118 with a thumb while the rest of the hand grasps around the casing 108.

Figure 2A:
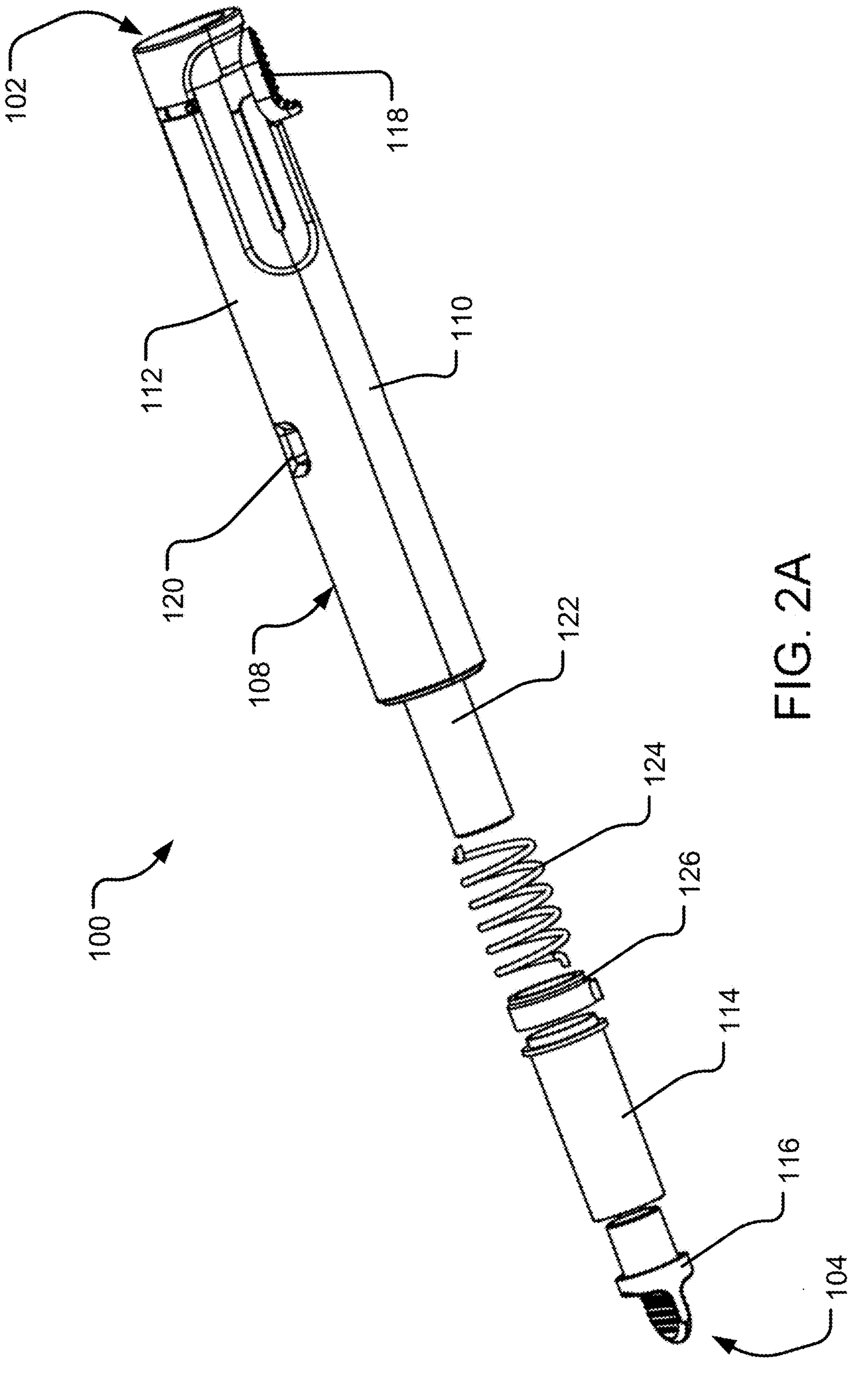
FIGS. 2A and 2B are, respectively, an isometric exploded view and a side view of the injector.
Figure 2B:
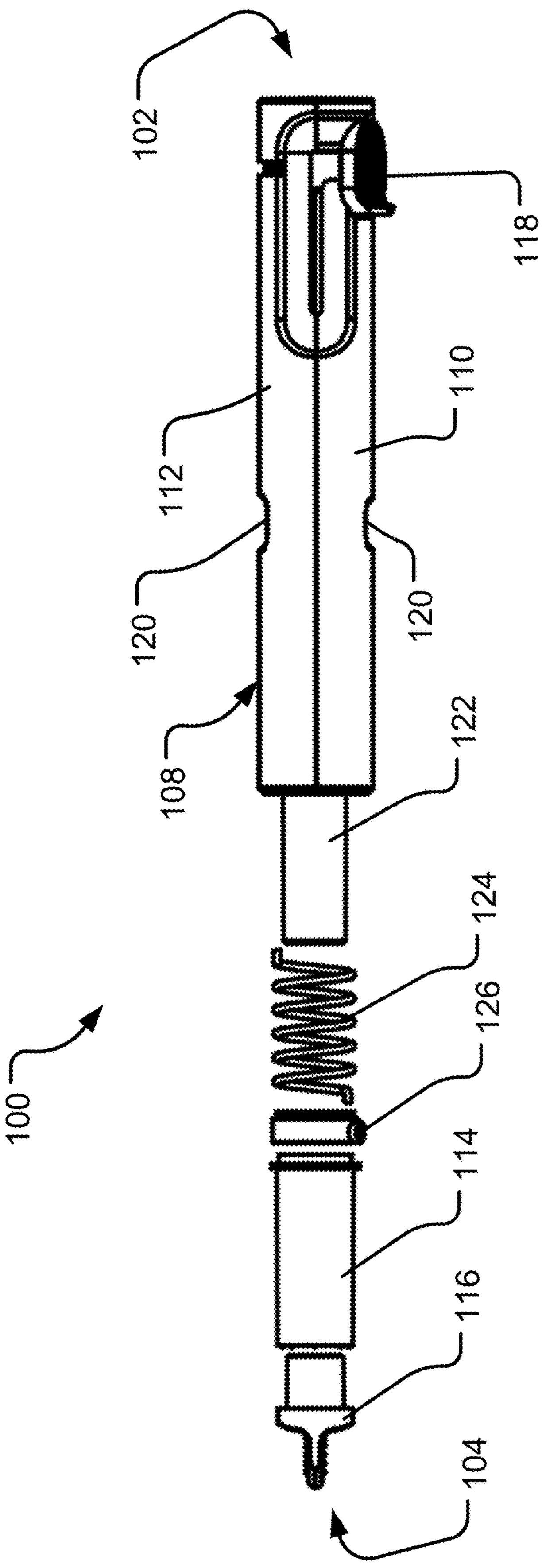

FIGS. 2A and 2B are, respectively, an isometric exploded view and a side view of the injector 100. In addition to the components already described and labeled on the figures, the injector 100 further includes cartridge 122 for receiving and securing the syringe within the casing 108, a biasing member 124 (e.g., a spring) in which biases the tube 114 in an extended position relative to the casing 108 and the cartridge 122, and a lock ring 126 that interfaces or engages with the biasing member 124 and with the tube 114.

Figure 3A:
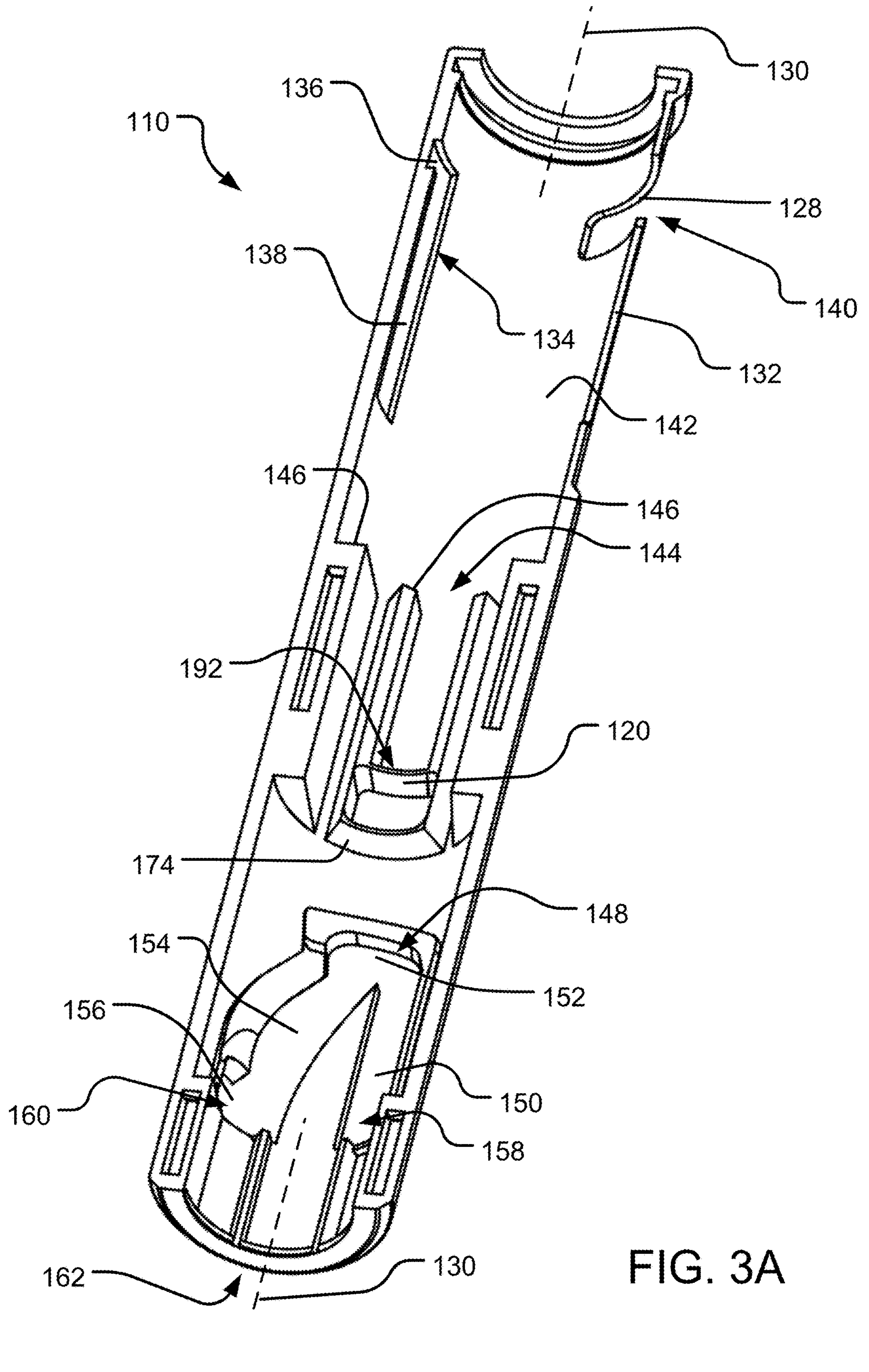
FIG. 3A is an isometric view of an inner side of a first casing.
Figure 3B:
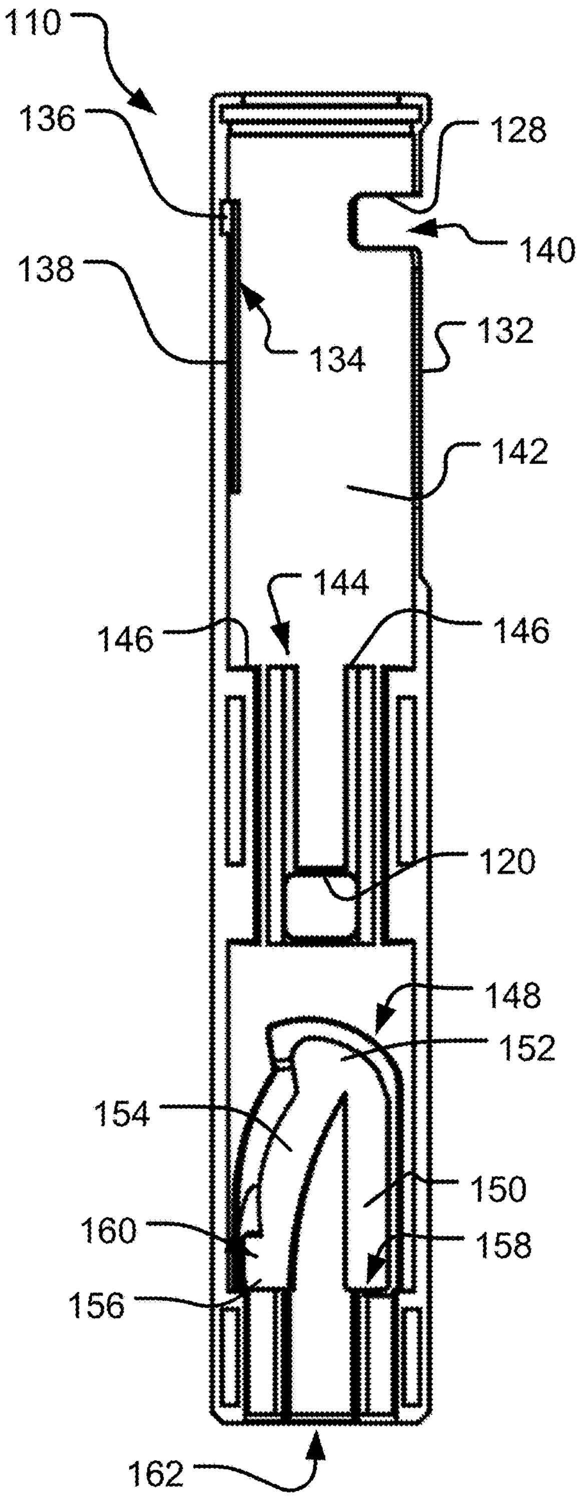
FIGS. 3B and 3C are, respectively, front view of the first casing showing the inner side thereof and a back view of the first casing showing the outer side thereof.
Figure 3C:
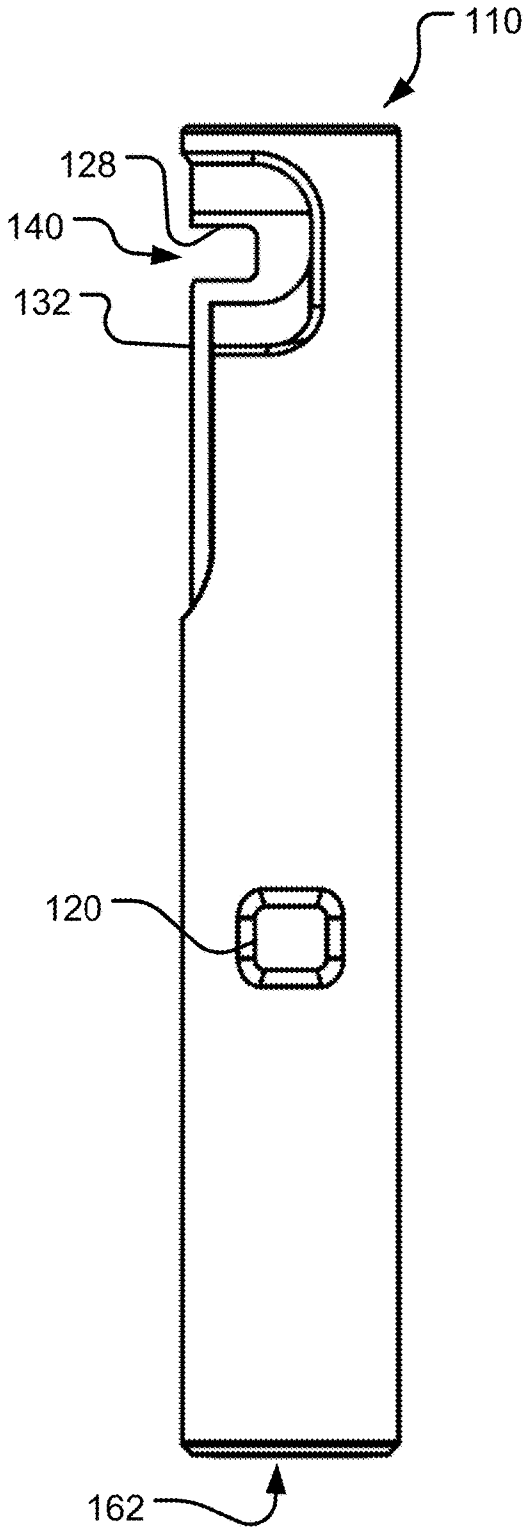
Figure 3D:
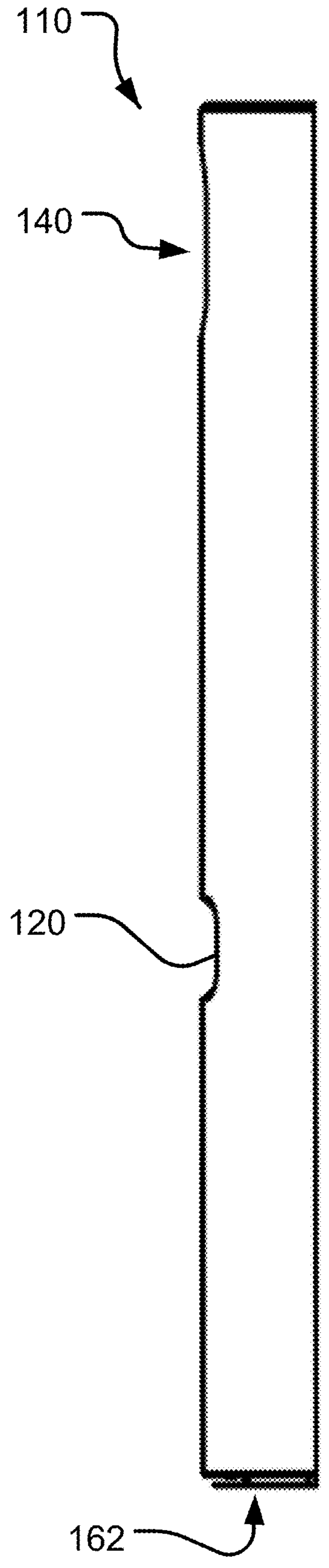
FIGS. 3D and 3E are, respectively, side views of the first casing from opposite sides.
Figure 3E:
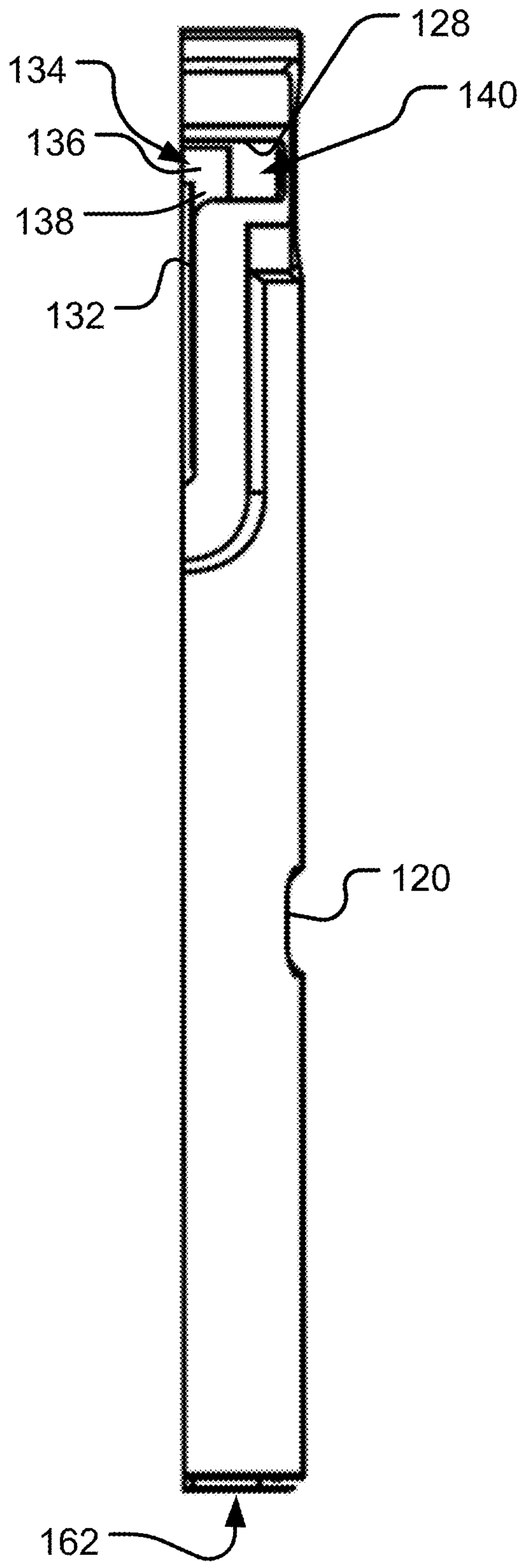
Figure 3G:
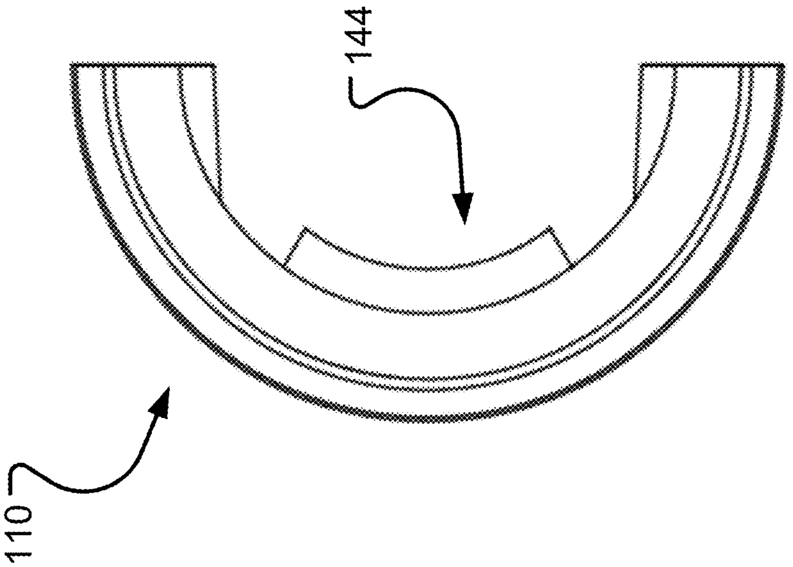
FIGS. 3F and 3G are, respectively, top and bottom views of the first casing.
Figure 3F:
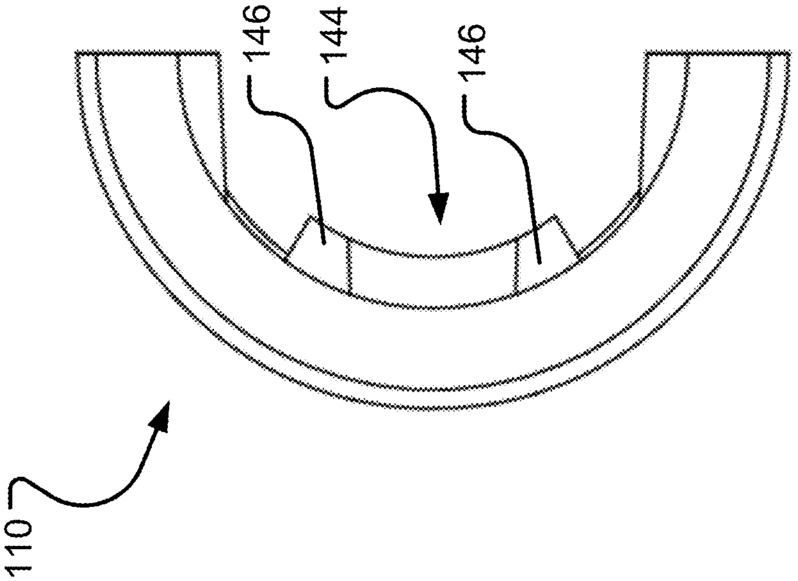

FIG. 3A is an isometric view of an inner side of a first casing 110, which couples with the second casing 112 (not shown) to form the full casing 108 (not shown). FIGS. 3B and 3C are, respectively, front view of the first casing 110 showing the inner side thereof and a back view of the first casing 110 showing the outer side thereof. FIGS. 3D and 3E are, respectively, side views of the first casing 110 from opposite sides. FIGS. 3F and 3G are, respectively, top and bottom views of the first casing 110.

As best seen in FIGS. 3A and 3B, at the proximal end (top of image), the first casing 110 includes a slider slot or opening 140 formed by a transverse section 128 (also referred to as a horizontal section) that extends generally perpendicular to the longitudinal axis 130 of the first casing 110. The transverse section 128 is contiguous with a longitudinal section 132 (also referred to as a vertical section) that is jointly defined by both the first casing 110 and the second casing. The transverse section 128 and the longitudinal section 132 are both through-holes defined through the casing 110, which permits a stem of the plunger slider 118 (not shown) to extend therethrough. More particularly, the transverse section 128 of the slider slot 140 permits transverse or horizontal rotation of the plunger slider 118, and then the longitudinal section 132 permits distal advancement or depression of the plunger slider 118, which causes dispensing of the substances from the syringe.

Figure 4A:
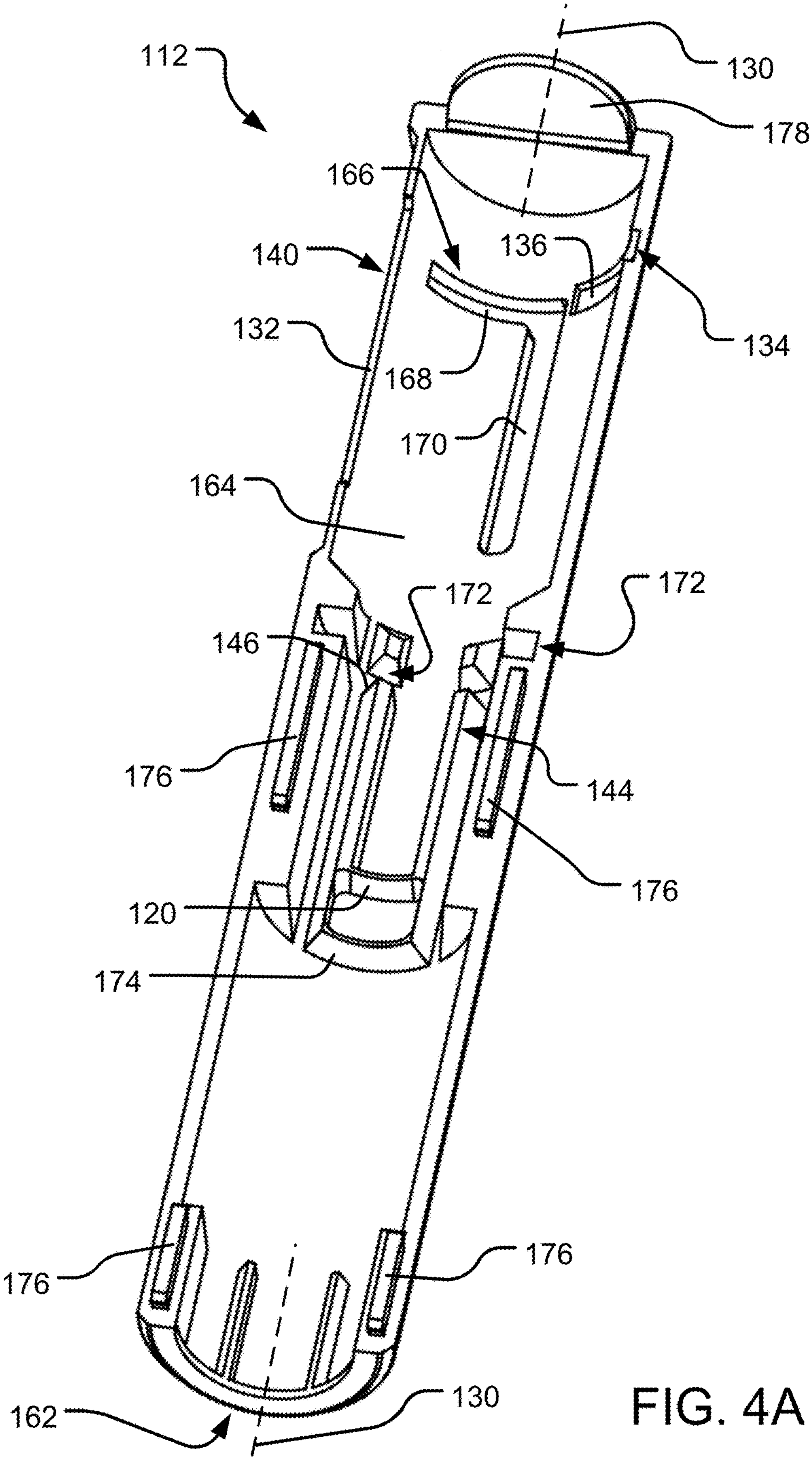
FIG. 4A is an isometric view of an inner side of a second casing.
Figure 4B:
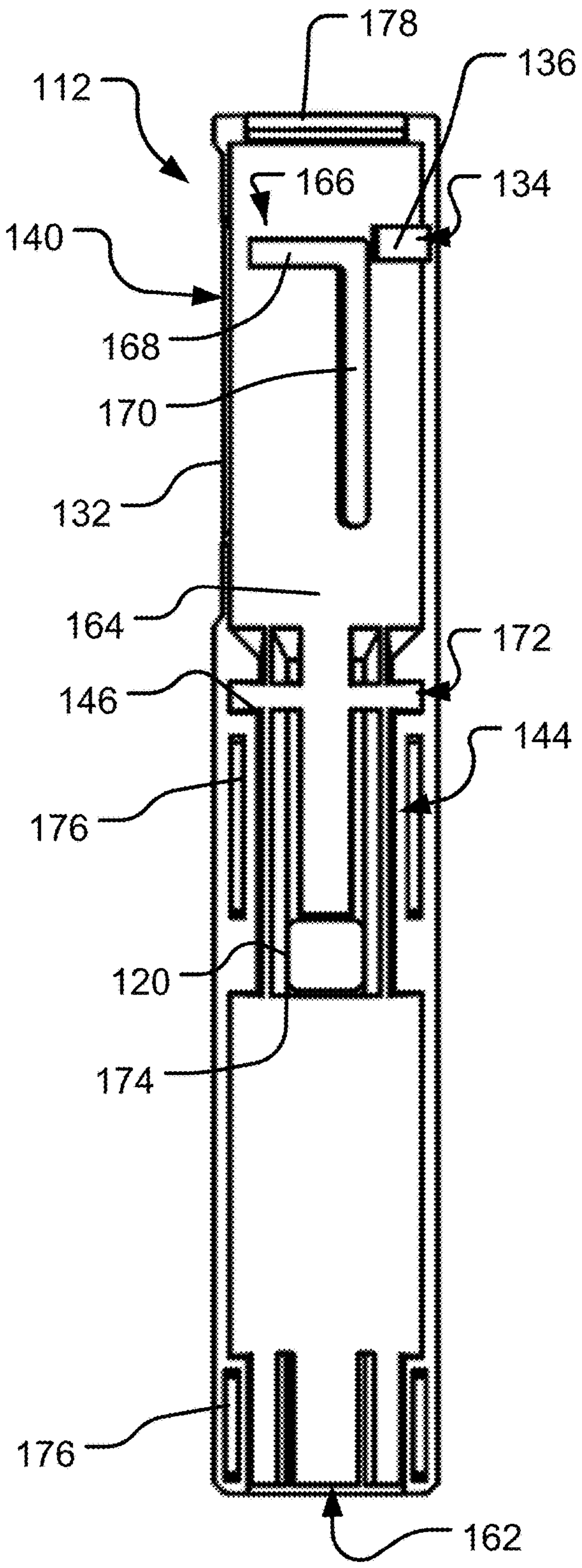
FIGS. 4B and 4C are, respectively, front view of the second casing showing the inner side thereof and a back view of the second casing showing the outer side thereof.

Also at the proximal end of the first casing 110 is a plunger guide recess 134 defined on an inner surface 142 of the first casing 110. The recess 134 does not extend through the entirety of the first casing 110. However, in alternative embodiments, the recess 134 may extend through an entirety of the first casing 110. The recess 134 includes a transverse section 136 (also referred to as a horizontal section) that is also partially defined on the second casing 112 (as shown in FIGS. 4A and 4B, among others). The transverse section 136 of the recess 134 is contiguous with a longitudinal section 138 (also referred to as a vertical section) extending along the longitudinal axis 130 of the first casing 110. The recess 134 is sized to receive and guide a protrusion on the plunger slider 118 (not shown in FIGS. 3A-3F). The plunger slider 118 is designed such that the protrusion and the stem of the plunger slider 118 are both guided by the slider slot 140 and recess 134 simultaneously to stabilize the plunger slider 118 during operation.

As seen in FIGS. 3A and 3B, a midsection of the first casing 110 includes projections 144 surrounding the window 120 and extending longitudinally along the midsection. The projections 144 include proximally-facing shoulders 146 sized and shaped to abut a portion of the syringe (not shown) therein. As seen in the figures, the first casing 110 includes recesses to facilitate coupling with the tabs on the second casing 112.

At the distal end, the first casing 110 includes a track or guide 148 defined within the inner surface 142. The track 148 is a recess defined within the inner surface 142 that is sized and shaped to receive and guide the protrusion on the lock ring 126 during retraction and extension of the tube 114 relative to the cartridge 122 and the first casing 110. The track 148 includes a starting point 158 and a terminus 160. The track 148 further includes a first longitudinal section 150 that is contiguous with a transverse section 152. The transverse section 152 is contiguous with a second longitudinal section 154 that includes an arched path. The second longitudinal section 154 is contiguous with a transverse locking section 156.

The biasing member 124 (not shown in FIGS. 3A and 3B), which is depicted as a spring, provides at least two functions. One, it biases the tube 114 in an extended position so as to shield the needle of the syringe. That is, the biasing member 124 exerts a longitudinal force distally on the tube 114. Second, the biasing member 124 rotationally biases the lock ring 126 so as to exert a rotational force from right-to-left in FIG. 3A. That is, the biasing member 124 is biased to advance in the transverse directions of the track 148. For instances, the rotationally biasing of the biasing member 124 causes the lock ring 126 to transition through the transverse section 152 and the transverse locking section 156 without additional force provided by the user. To overcome the longitudinal force of the biasing member 124, the user applies a proximal force on the tube 114. This causes the protrusion of the lock ring 126 to travel along the first longitudinal section 150. Once, the protrusion is at the terminus of the first longitudinal section 150, the lock ring 126 automatically rotates through the transverse section 152 via the rotationally biasing force of the biasing member 124. Then, as the user relieves proximal-directed force on the tube 114, the tube 114 extends, which causes the biasing member 124 to extend. This causes the protrusion of the lock ring 126 to travel along the second longitudinal section 154 to its terminus. At its terminus, the lock ring 126 automatically rotates into and through the transverse locking section 156 to its terminus. At the terminus 160 of the track 148, the biasing member 124 rotationally biases the protrusion of the lock ring 126 into an end wall. Longitudinal movement of the lock ring 126 is restricted as well given the end wall is only slightly larger than the protrusion of the lock ring 126. Thus, once the protrusion of the lock ring 126 has travelled from start 158 to the terminus 160, the lock ring 126 is locked at the terminus 160 of the track 148. Since the lock ring 126 is coupled to the tube 114, this mean that when the lock ring 126 is locked at the terminus 160 of the track, the tube 114 is locked in the extended position and is restrained from transitioning back to the retracted position. At the distal end, the first casing 110 includes a distal opening 162 that is formed by the mating of the first and second casings 110, 112.

Figure 4C:
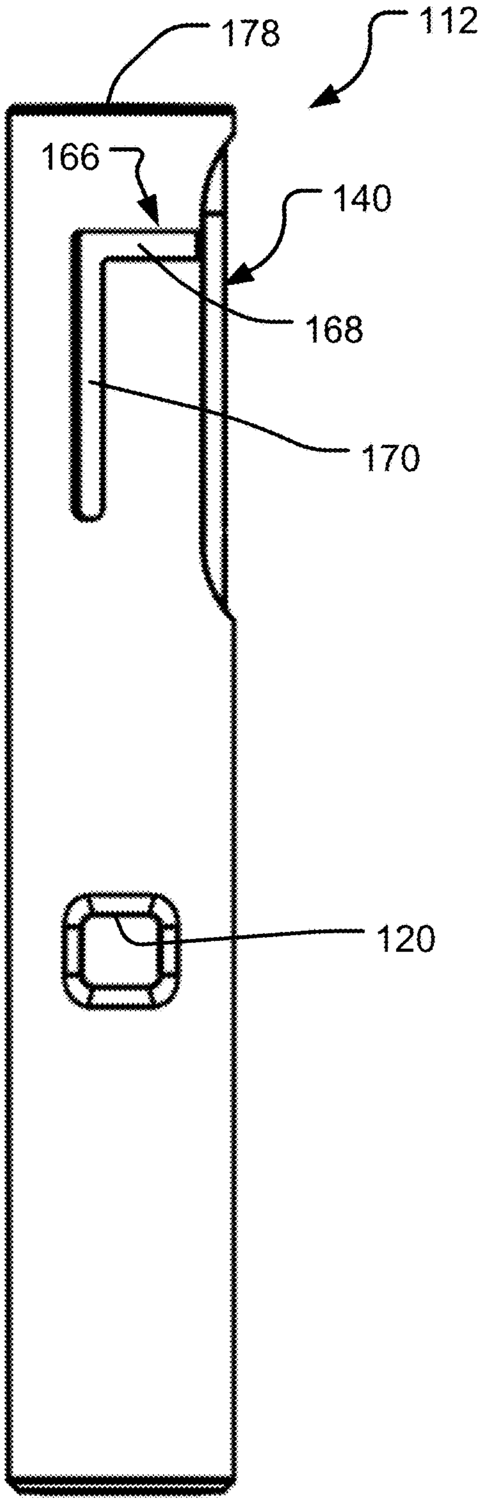
Figure 4D:
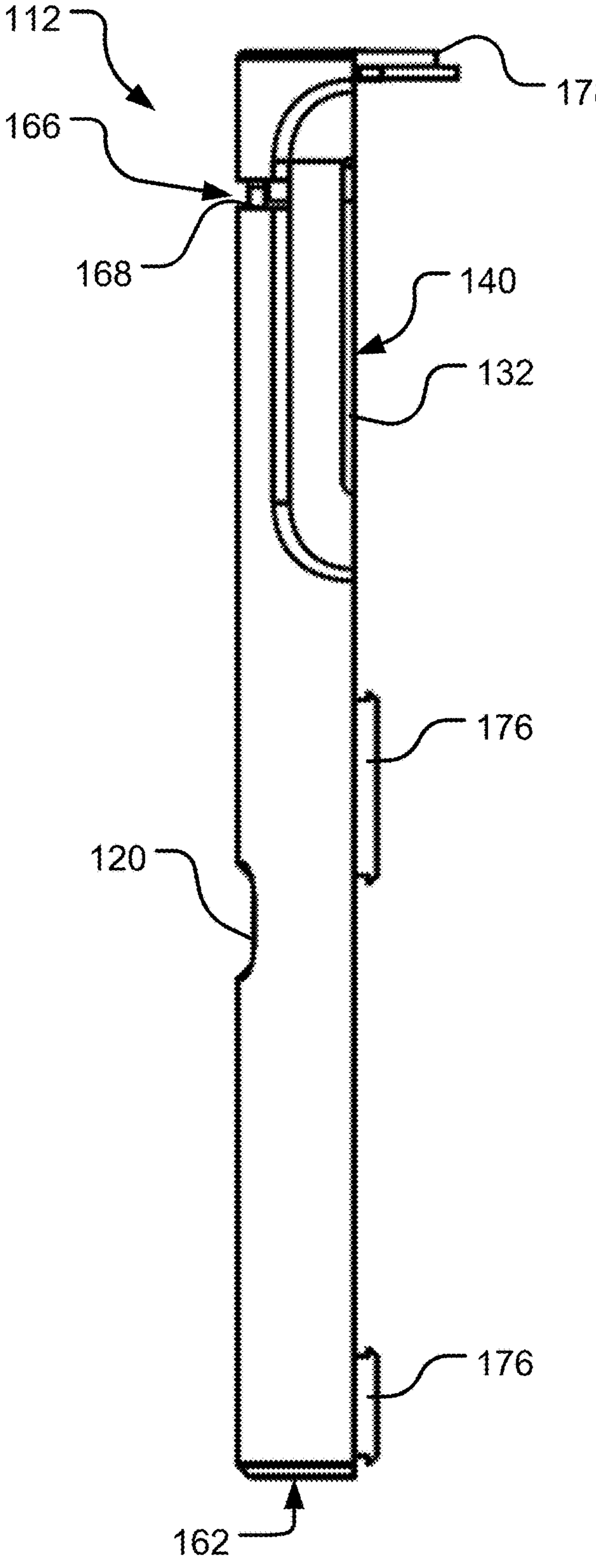
FIGS. 4D and 4E are, respectively, side views of the second casing from opposite sides.
Figure 4E:
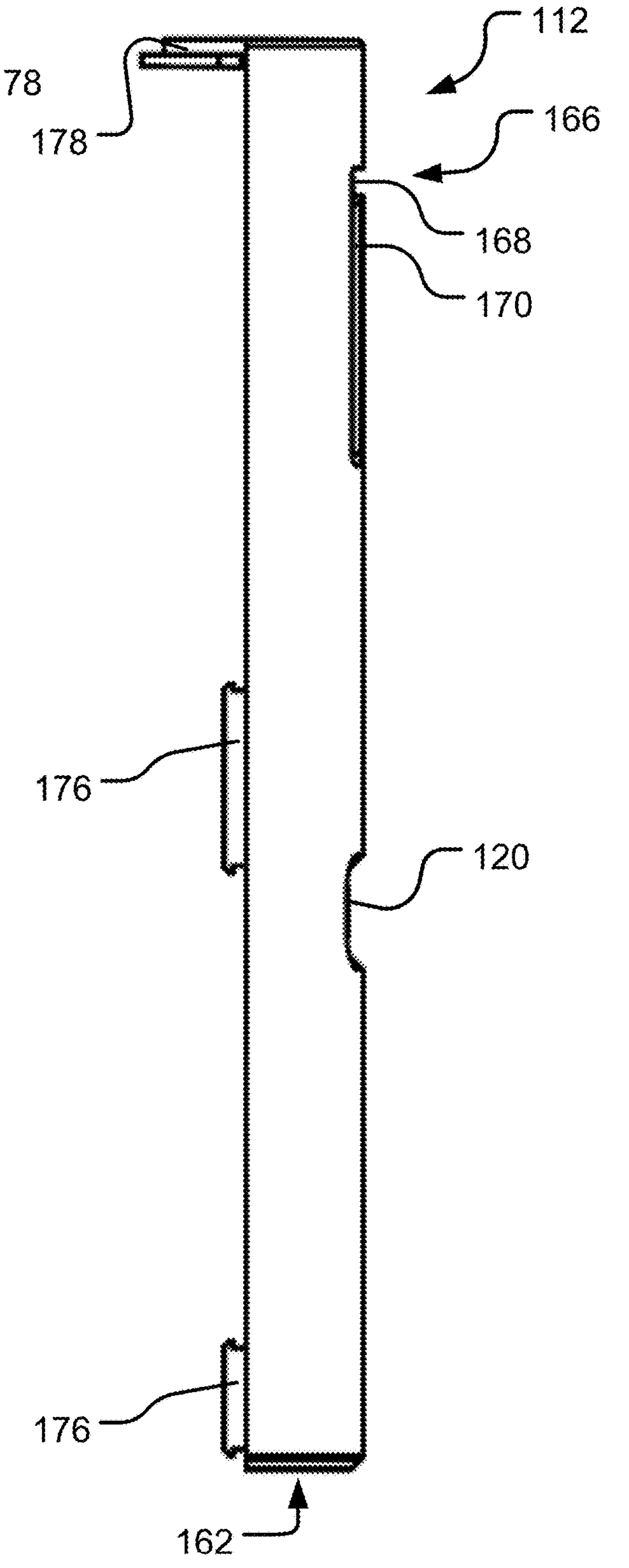
Figure 4G:
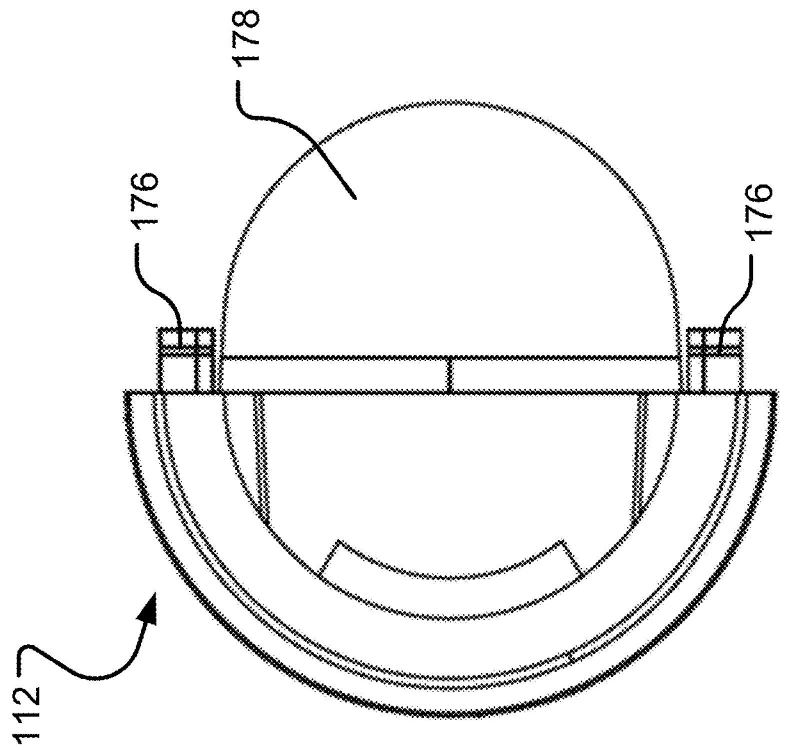
FIGS. 4F and 4G are, respectively, top and bottom views of the second casing.
Figure 4F:
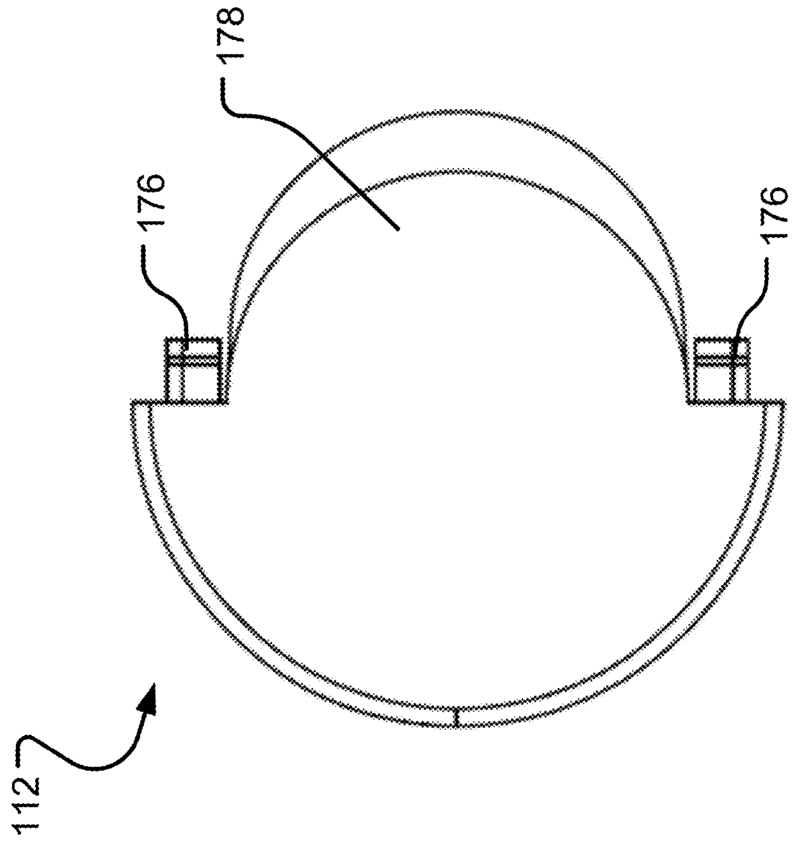

FIG. 4A is an isometric view of an inner side of a second casing 112. FIGS. 4B and 4C are, respectively, front view of the second casing 112 showing the inner side thereof and a back view of the second casing 112 showing the outer side thereof. FIGS. 4D and 4E are, respectively, side views of the second casing 112 from opposite sides. FIGS. 4F and 4G are, respectively, top and bottom views of the second casing 112.

As best seen in FIGS. 4A and 4B, at the proximal end of the second casing 112 (top of image), the longitudinal section 132 of the slider slot 140 is partly formed on the second casing 112. As described with reference to FIGS. 3A-3G, the slider slot 140 is formed by a transverse section 128 that extends generally perpendicular to the longitudinal axis 130 of the first casing 110. The transverse section 128 is contiguous with the longitudinal section 132 that is jointly defined by both the first casing 110 and the second casing 112. Similarly, a portion of the transverse section 136 of the plunger guide recess 134 is defined on an inner surface 164 of the second casing 112, whereas another portion of it is defined on the inner surface 142 of the first casing 110. The recess 134 does not extend through the entirety of the second casing 112. However, in alternative embodiments, the recess 134 may extend through an entirety of the second casing 112. The recess 134 includes the transverse section 136 that is also partially defined on each of the first and second casings 110, 112. The transverse section 136 of the recess 134 is contiguous with a longitudinal section 138 extending along the longitudinal axis 130 of the first casing 110. The recess 134 is sized to receive and guide a protrusion on the plunger slider 118 (not shown in FIGS. 4A-4G).

At the proximal end of the second casing 112 is a plunger guide slot or opening 166 extending through the second casing 112. The plunger guide slot 166 includes a transverse section 168 extending generally perpendicular to the longitudinal axis 130 (also described as extending horizontally) of the second casing 112. The transverse section 168 is contiguous with a longitudinal section 170 that extends longitudinally along the second casing 112 (also described as extending vertically). The plunger guide slot 166 is sized and shaped to received and guide a protrusion on the plunger slider 118. Unlike the plunger guide recess 134, the plunger guide slot 166 extends through the entire sidewall of the second casing 112. This provides a robust guiding alignment of the plunger slider 118 as well as a visual indication or verification of the location of the plunger slider 118 relative to the casing 108.

At a midsection of the second casing 112 are the protrusions 144 extending inwardly towards a center of the casing 108. The protrusions 144 support and centrally position the cartridge as will be explained subsequently. The second casing 112 also includes recesses 172 defined within the protrusions 144 for receiving and securing the flange of the barrel of a syringe, which is in turn supported in the cartridge 122. With the syringe barrel held in place by the recesses 172 (and generally held in a fixe position relative to the casing 108), the plunger slider 118 operates to distally depress the plunger of the syringe into the barrel and, thus, dispense the substance (e.g., drug) from the barrel of the syringe.

On a distal side of the protrusions 144 are distally-facing shoulders 174 that are oppositely positioned from the proximally-facing shoulders 146. The distally-facing shoulders 174 are sized and shaped to abut a portion of the cartridge 122 and to restrict proximal movement of the cartridge 122 within the casing 108.

Referring back to the proximal end, the second casing 112 includes a proximal cap 178 that encapsulates the proximal end of the casing 108 when the first and second casings 110, 112 are coupled together. At the midsection and at the distal end, the second casing 112 includes tabs 176 that jut outwards and are sized and shaped to couple with corresponding recesses on the first casing 110.

Figure 5A:
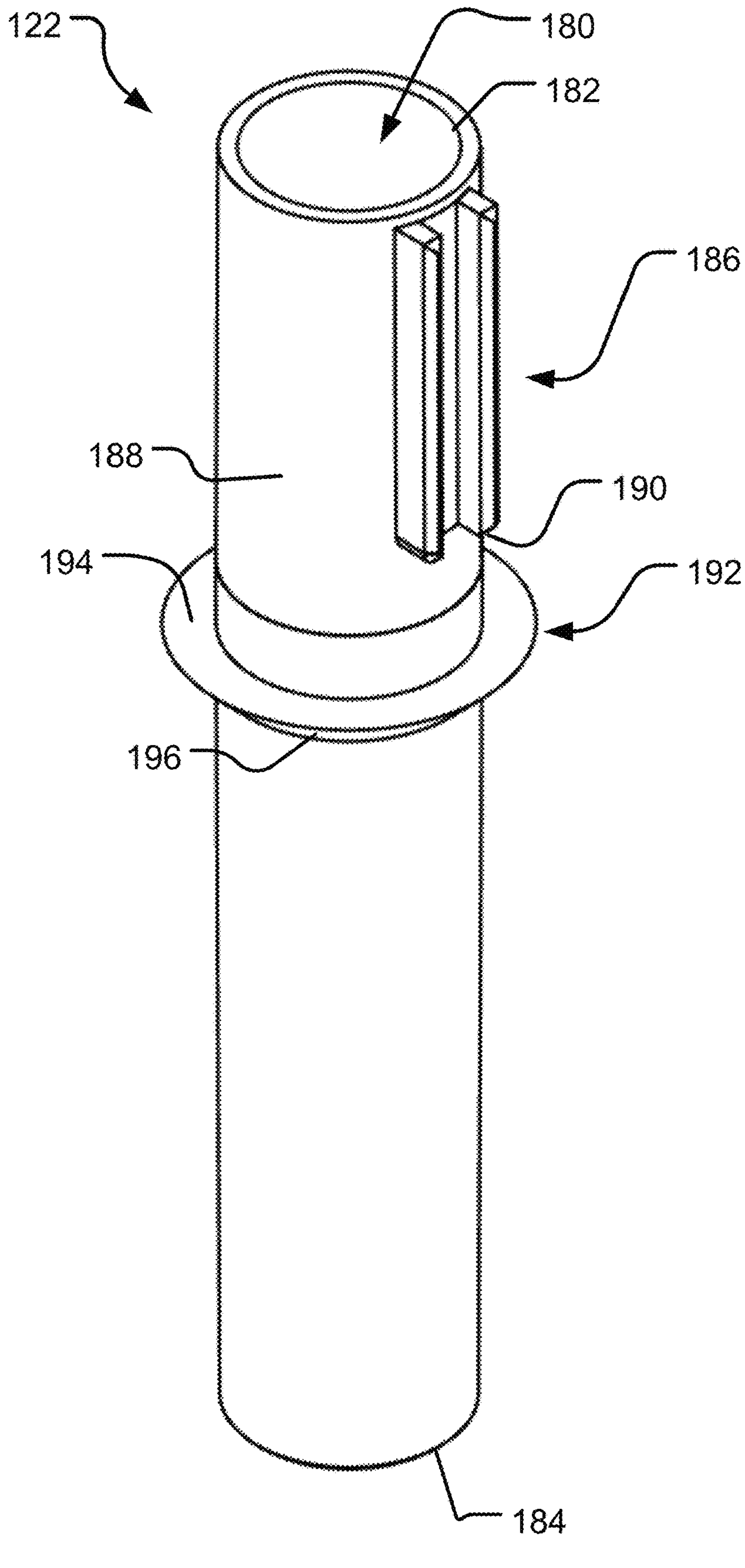
FIG. 5A is an isometric view of a cartridge for supporting a syringe within the injector.
Figure 5B:
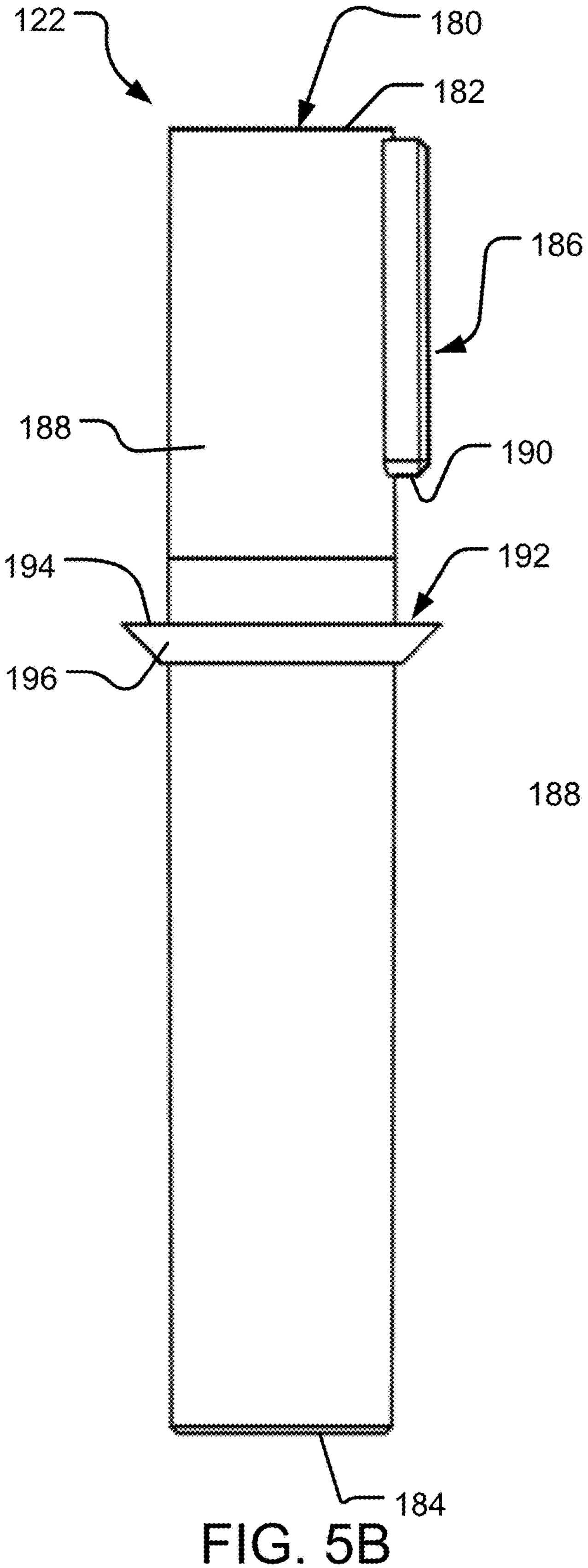
FIGS. 5B and 5C are, respectively, side views of the cartridge from two different rotational orientations.
Figure 5C:
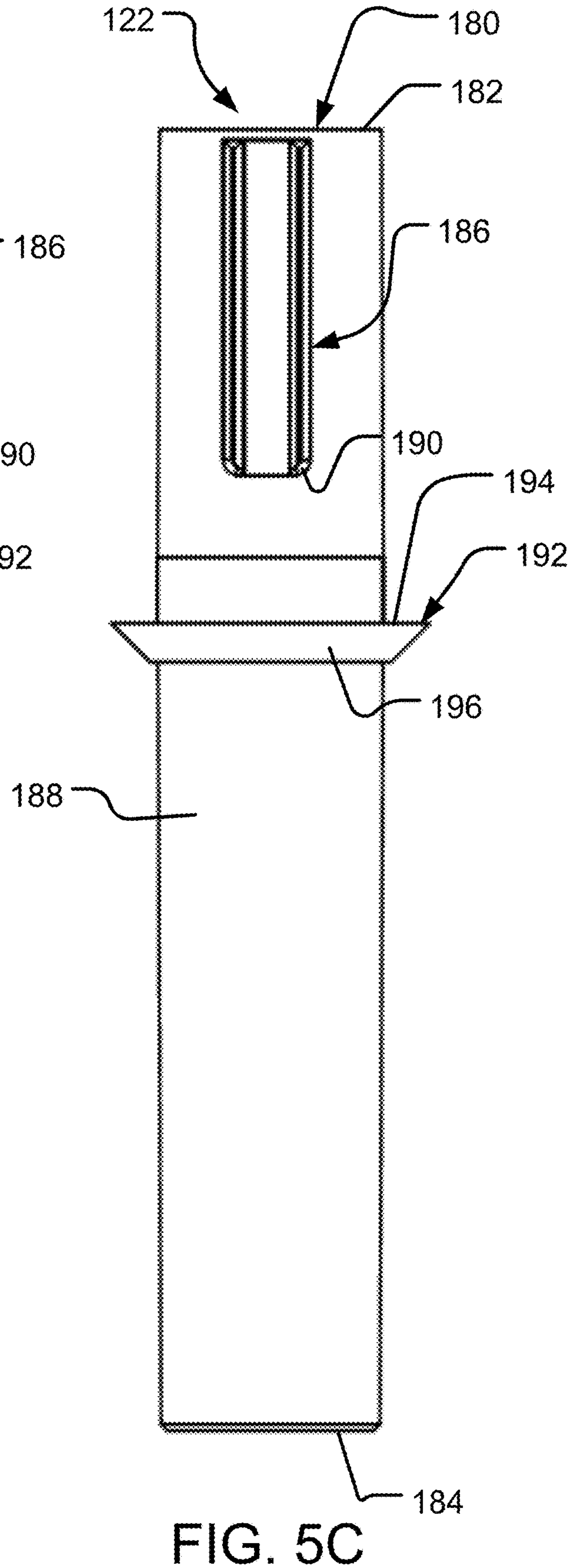
Figure 5D:
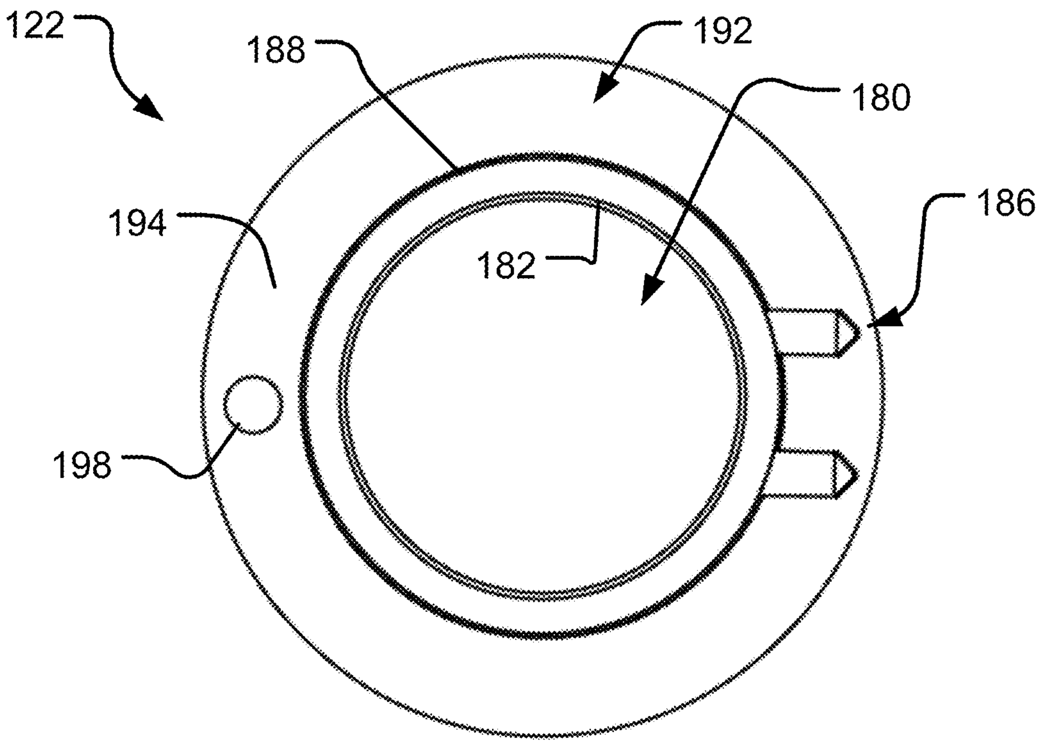
FIGS. 5D and 5E are, respectively, top and bottom views of the cartridge.
Figure 5E:
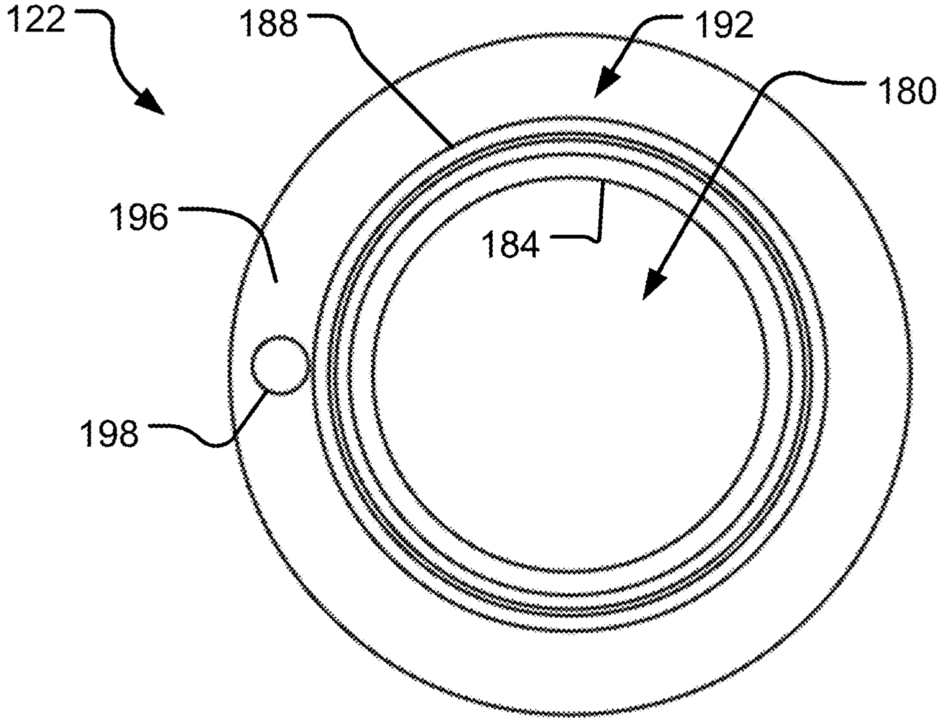

FIG. 5A is an isometric view of the cartridge 122 for supporting a syringe within the casing 108 (not shown) of the injector 100 (not shown). FIGS. 5B and 5C are, respectively, side views of the cartridge 122 from two different rotational orientations. FIGS. 5D and 5E are, respectively, top and bottom views of the cartridge 122. As seen in the figures, the cartridge 122 is a tubular body having a passageway 180 extending from a proximal opening 182 at the proximal end (top of image in FIG. 5A) to a distal opening 184 at the distal end (bottom of image in FIG. 5A). The cartridge 122 includes a pair of alignment fins 186 extending outward from the outer surface 188 of the cartridge 122. The alignment fins 186 include distal surfaces 190 for abutting against a proximally-facing surface of the casing 108 to inhibit distal advancement. In certain instances, the alignment fins 186 may be a single fin or more than a pair of fins. When inserted into the casing 108, the alignment fits 186 are sized and shaped to be received within the protrusions 144 on the first casing 110. And, the distal surfaces 190 abut an upper wall 192 (as seen in FIG. 3A) of the protrusions 144 that define a part of the casing for the window 120.

At a midsection of the cartridge 122 is a annular flange 192 in the shape of a frustoconical ring with a proximally-facing surface 194 that is generally perpendicular to a longitudinal axis of the cartridge 122. The proximally-facing surface 194 is joined by a distal-facing surface 196 that is angled or beveled so as to angle proximally. When the cartridge 122 is positioned within the casing 108, the annular flange 192 abuts against the distally-facing shoulders 174 of the protrusions 144. This abutment prevents proximal movement of the cartridge 122 within the casing 108. As such, once inserted into the casing 108, the cartridge is prevented from both proximal and distal movement therein via interaction of the annular flange 192 with the distally-facing shoulders 174 of the protrusions 144 (proximal movement) and interaction of the alignment fins 186 with the upper wall 192 of the protrusions that define part of the casing of the window 120.

As seen in FIGS. 5D and 5E, the annular flange 192 includes a through-hole 198 extending from the distal surface 196 to the proximal surface 194. The through-hole 198 is sized to receive an end of the biasing member 124 (e.g., spring) (not shown in FIGS. 5D and 5E). As described previously, the biasing member 124 exerts both a longitudinal force on the lock ring 126 and tube 114 in an outward or extended position, and a rotational force on the lock ring 126. The biasing member 124 is coupled to the cartridge 122 via the through-hole 198, and the cartridge 122 is fixed in its position within the casing 108 as described previously.

Figure 6A:
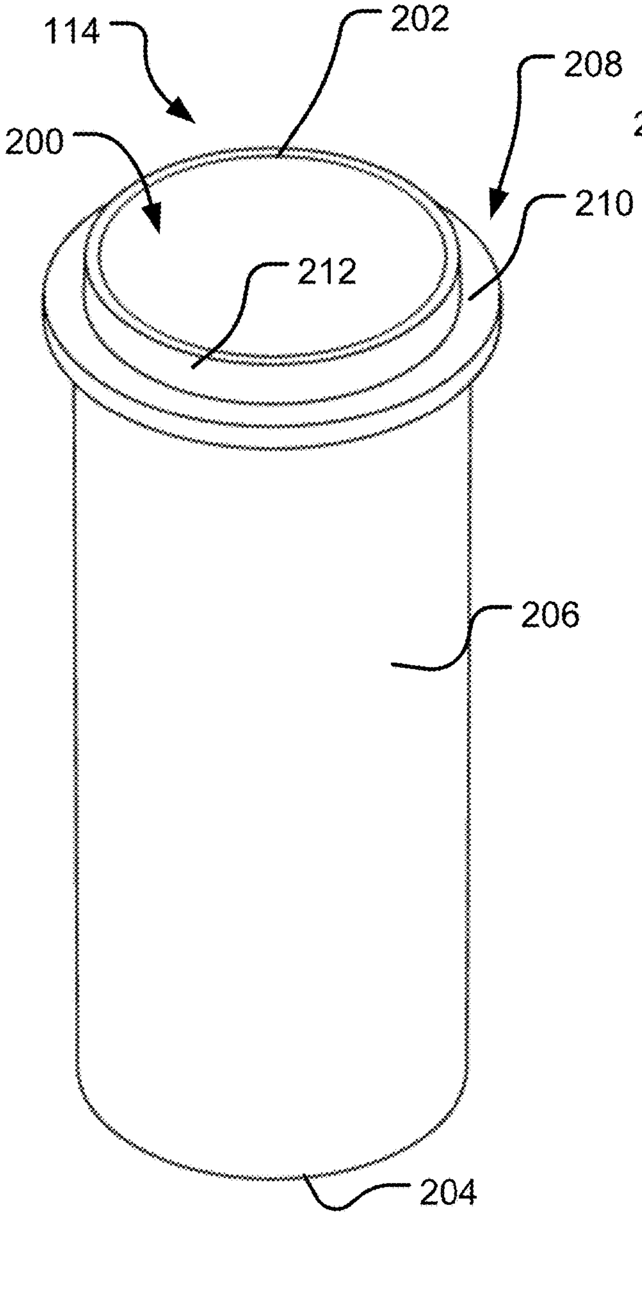
FIGS. 6A and 6B are, respectively, an isometric view and a side view of a distal tube of the injector.
Figure 6B:
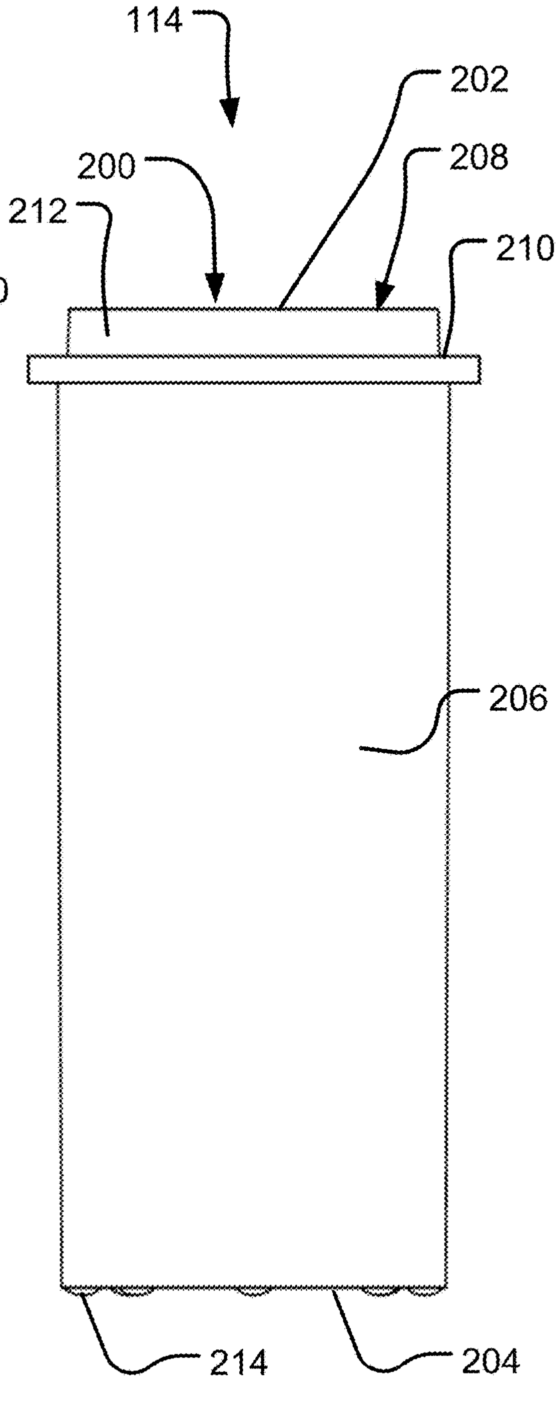
Figure 6C:
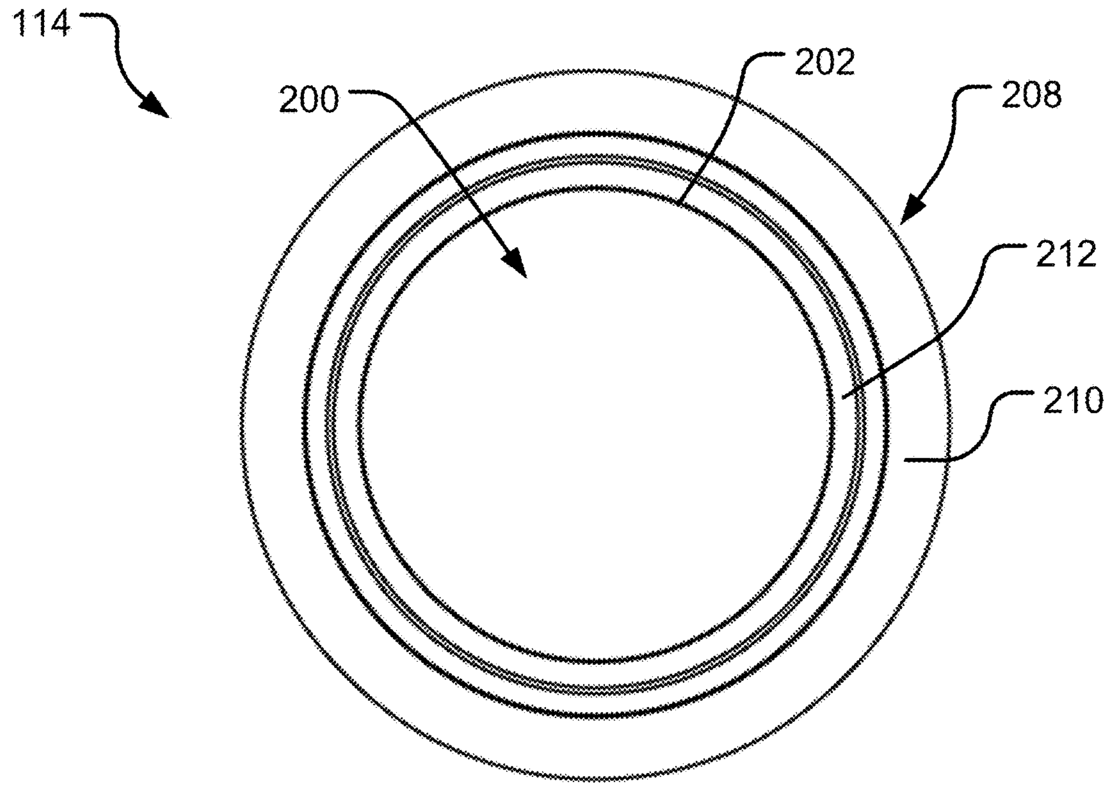
FIGS. 6C and 6D are, respectively, top and bottom views of the distal tube.
Figure 6D:
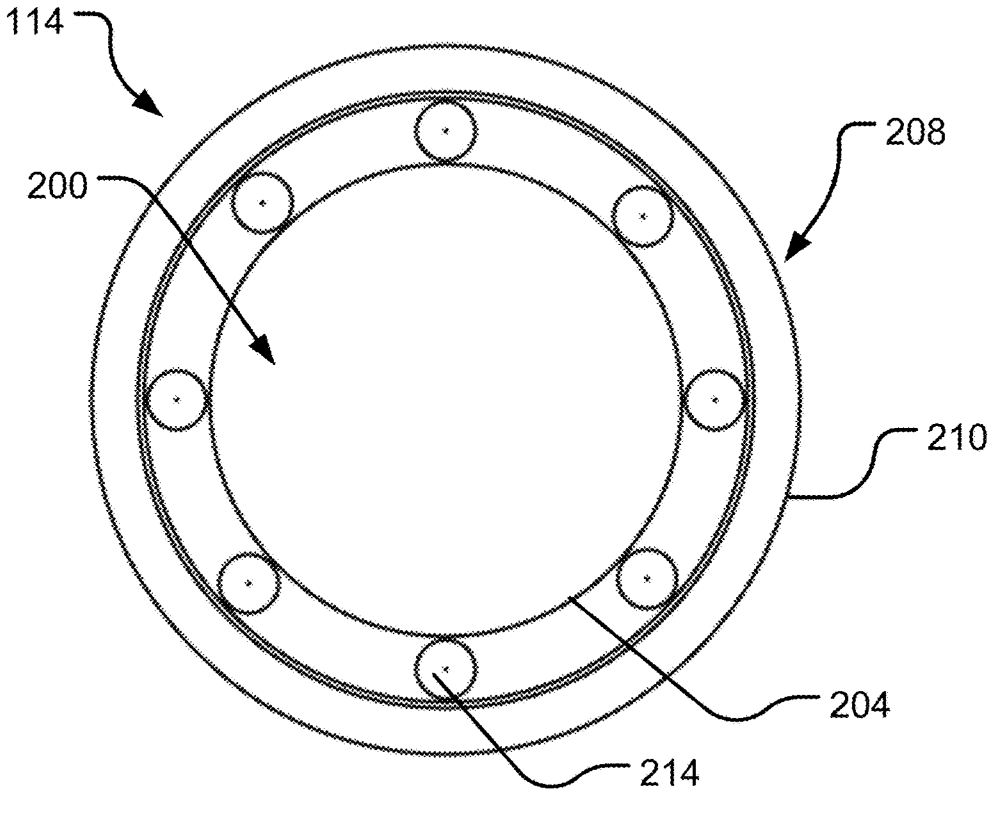

FIGS. 6A and 6B are, respectively, an isometric view and a side view of the tube 114 of the injector 100. FIGS. 6C and 6D are, respectively, top and bottom views of the tube 114. As seen in the figures, the tube 114 includes a passageway 200 extending from a proximal opening 202 to a distal opening 204. The tube 114 includes a tubular surface 206 and coupling structure 208 at the proximal end. The coupling structure 208 includes an annular rim 210 and a proximal projection 212. The coupling structure 208 is sized to receive the lock ring 126 thereon. That is, the lock ring 126 may be fitted over the proximal projection 212 in a friction fit arrangement or they may be affixed together (e.g., mechanical or chemical fastener). The distal end of the tube includes nubs 214 protruding distally from the distal rim of the tube 114. The nubs 214 abut the skin of the user when the injector 100 is applied to the patient. The nubs 214 function sensory stimulation to the user so the fear of needlestick is reduced.

Figure 7A:
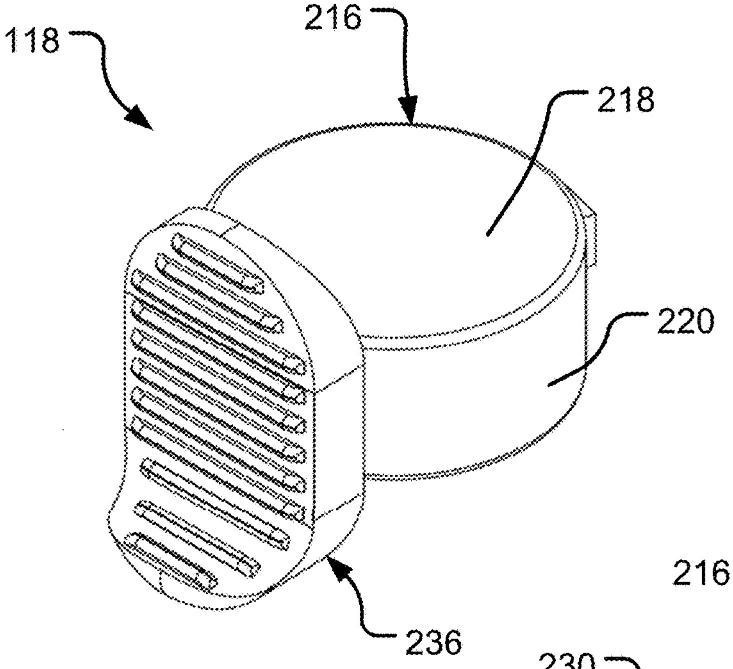
FIGS. 7A-7E are, respectively, an isometric view, two side views, a top view, and a bottom view of a plunger slider.
Figure 7B:
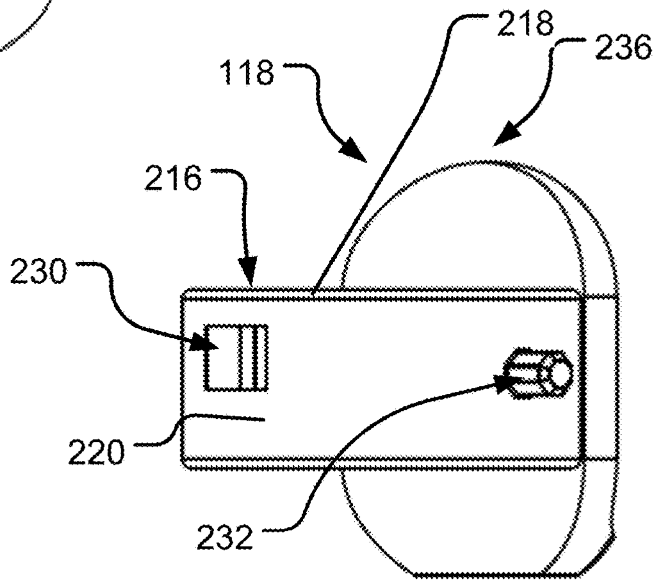
Figure 7C:
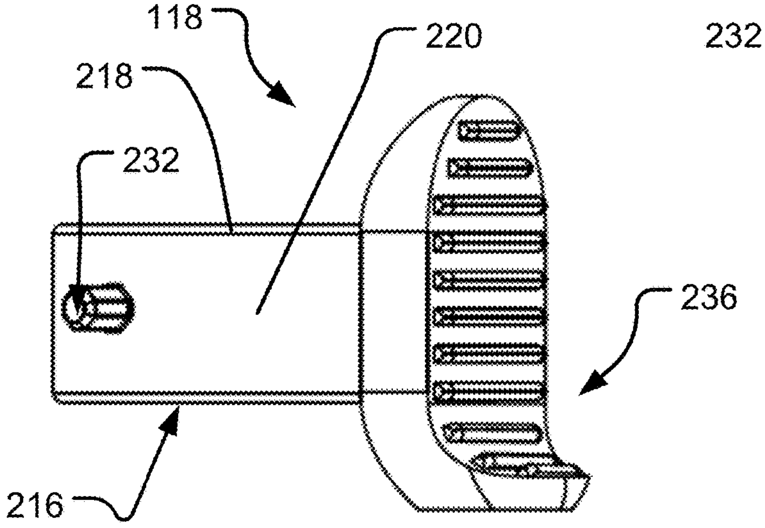
Figure 7D:
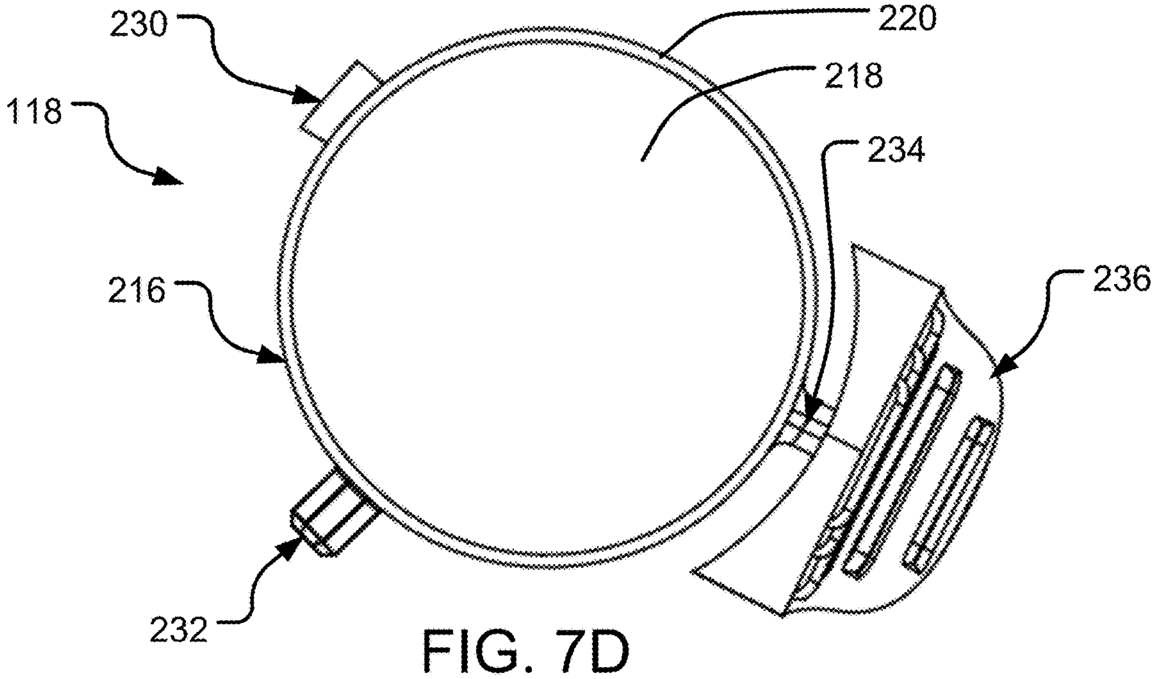
Figure 7E:
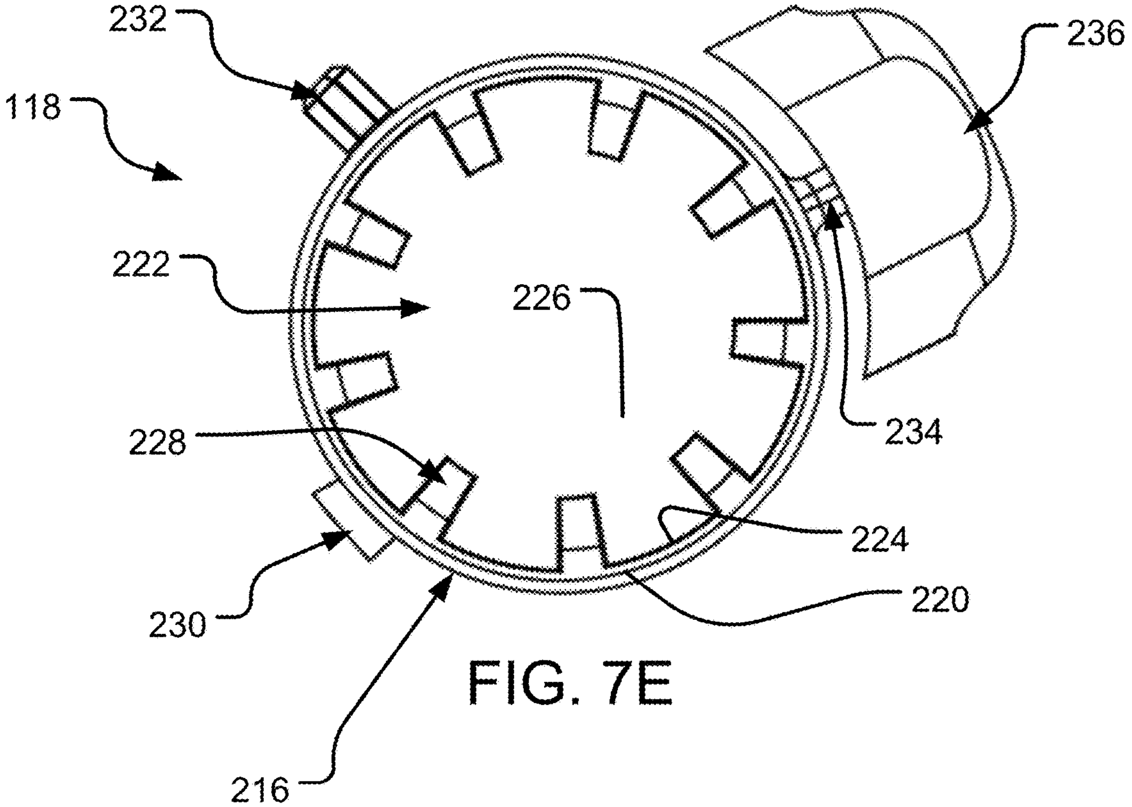

FIGS. 7A-7E are, respectively, an isometric view, two side views, a top view, and a bottom view of a plunger slider 118. As seen in the figures, the plunger slider 118 includes a cap 216 having a top surface 218, and a cylindrical sidewall 220 coupled to the top surface 218. A cavity 222, as seen in FIG. 7E, is defined between the sidewall 220 and the top surface 218 for receiving the end of the plunger of the syringe therein. Continuing with FIG. 7E, a series of inwardly extending projections 228 extend from an inner surface 224 of the sidewall 220 to the underside 226 of the cap 216. The series of projections 228 centrally position the plunger of the syringe so it does not move off-center.

Coupled to and extending outward from the sidewall 220 of the cap 216 are first and second projections 230, 232. The first projection 230 is in the form of a four sided projection that is sized and shaped to fit and slide within the recess 134 defined partially on the first and second casings 110, 112. The second projection 232 is in the form of a post that is sized and shaped to fit and slide within the plunger guide slot 166 defined within the second casing 112.

As best seen in FIGS. 7D and 7E, the plunger slider 118 includes an engagement structure 236 (thumb slider) coupled to the cap 216 via a stem 234. The engagement structure 236 includes ridges for grip and a radially projecting portion for grip as well. The engagement structure 236 may include alternative shapes and sizes. The embodiment shown in the drawings is merely exemplary of an engagement structure 236. The cap 216 is sized and shaped to fit within the casing 108 such that: the stem 234 extends through the plunger slider slot 140 defined within the casing 108; the first projection extends into the plunger slider recess 134 of the casing 108; and the second projection extends into the plunger guide slot 166 of the casing 108. In this way, the plunger slider 118 is guided by three guides as a user rotates the plunger slider 118 and then applies distal pressure on the engagement structure 236. The three guides ensure correct alignment of the plunger slider 118 and consistent application of the injector 100 generally.

Figures 8A, 8B, 8C:
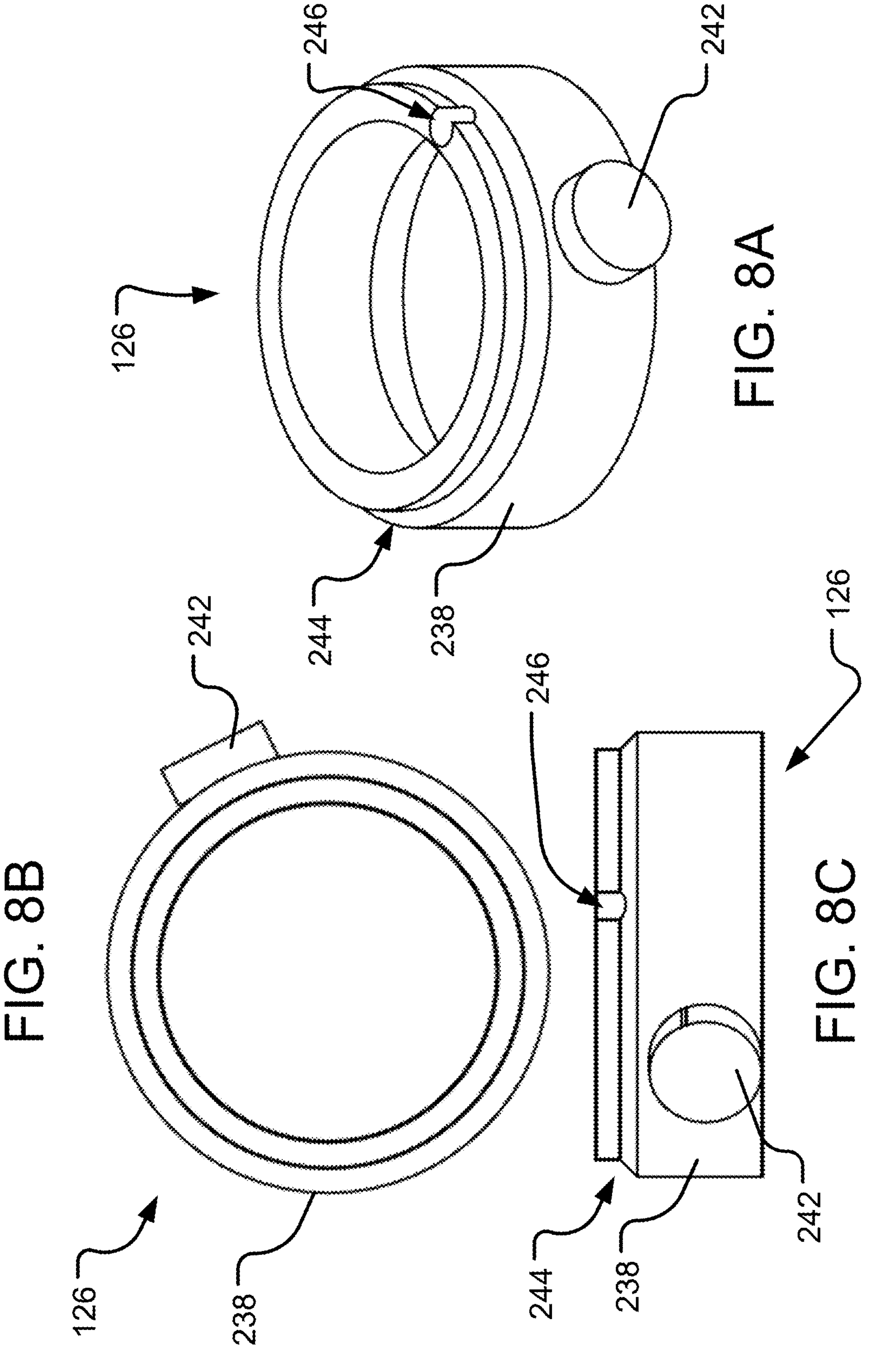
FIGS. 8A-8C are, respectively, an isometric view, a bottom view, and a side view of a lock ring.

FIGS. 8A-8C are, respectively, an isometric view, a bottom view, and a side view of the lock ring 126. The lock ring 126 includes a cylindrical sidewall 238 with a through-hole 240 extending from a proximal end (top of lock ring 126 in FIGS. 8A and 8C) to the distal end. Extending outward from the sidewall 238 in a direction perpendicular to a longitudinal axis of the lock ring 126 is a protrusion or post 242 of cylindrical shape. The protrusion 242 is sized and shaped to be received within and be guided by the track 148 on the inner surface 142 of the first casing 110 as described previously. At the proximal end of the lock ring 126 is an incut section 244 with a bore hole 246 defined therein for receiving an end of the biasing member or spring 124. It is noted that the lock ring 126 may be integrally formed with the distal tube 114. That is, the lock ring 126 and the distal tube 114 may be a single piece construction.

Figure 9:
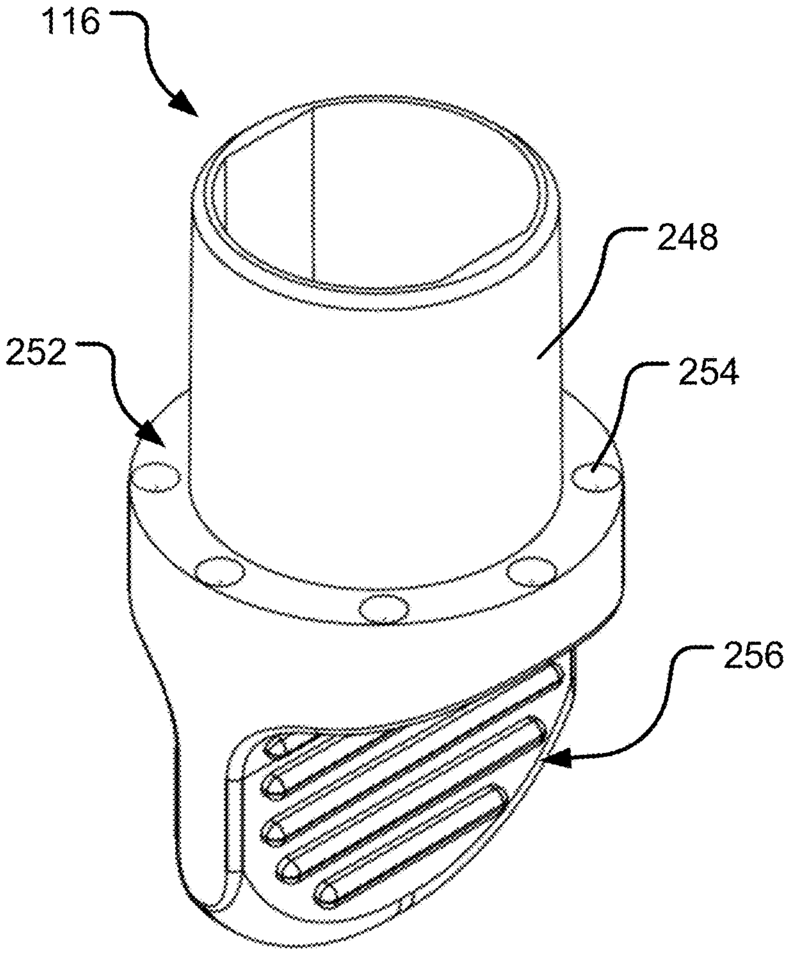
FIG. 9 is an isometric view of a distal cap of the injector.

FIG. 9 is an isometric view of a distal cap 116 of the injector 100. The cap 116 includes tube 248 having an outer cylindrical surface 250 sized to fit within the tube 114 and be retained therein. At the base of the tube 248 is a flange 252 with series of divots 254 for receiving the nubs formed on the distal end of the tube 114 when the tube 114 is mated with the cap 116. Extending distally from the flange 252 is a dual-sided structure with ridges 256 for grasping by the user. The internal sides of the tube 248 include surfaces to closely abut and couple to a conventional syringe cap. Thus, removal of the cap 116 from coupling with the tube 114 also removes the syringe cap from the syringe.

Figure 10:
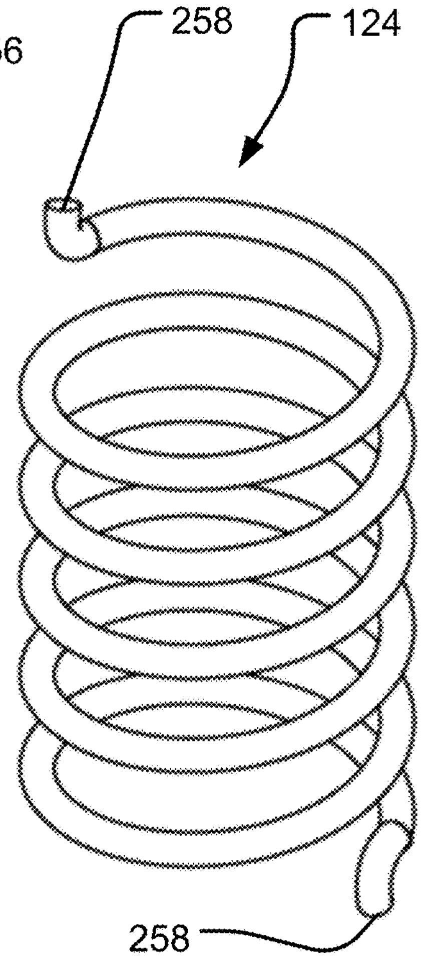
FIG. 10 is an isometric view of a compression spring of the injector.

FIG. 10 is an isometric view of the biasing member 124 of the injector 100. As seen in the figure, the biasing member 124 is a spring, and, more particular, a compression spring. The biasing member 124 includes a pair of ends 258. One of the pair of ends 258 is to be received within the through-hole 198 of the annular flange 192 of the cartridge 122, and the opposite end 258 of the biasing member 124 is received within the through-hole 246 of the lock ring 126. As described previously, during use, the biasing member 124 exerts a biasing force on the lock ring 126, which is fitted to the proximal end of the tube 114. The biasing force causes the tube 114 to be biased in an extended position covering the needle of the syringe. The biasing member 124 is also assembled with a rotational bias such that the lock ring 126 is rotationally forced to travel through the track 148 defined on the first casing 110. The rotational biasing of the lock ring 126 causes the locking of the lock ring 126 and coupled tube 114 upon a single retraction and subsequent extension of the tube 114 relative to the casing 108. Stated differently, the injector 100 is designed to permit a single retraction of the tube 114 to expose the needle of the syringe. And, upon re-extension of the tube 114 following retraction, the rotational bias of the biasing member 124 causes locking of the tube 114 in an extended position shielding the needle.

Figures 11A, 11B, 11C:
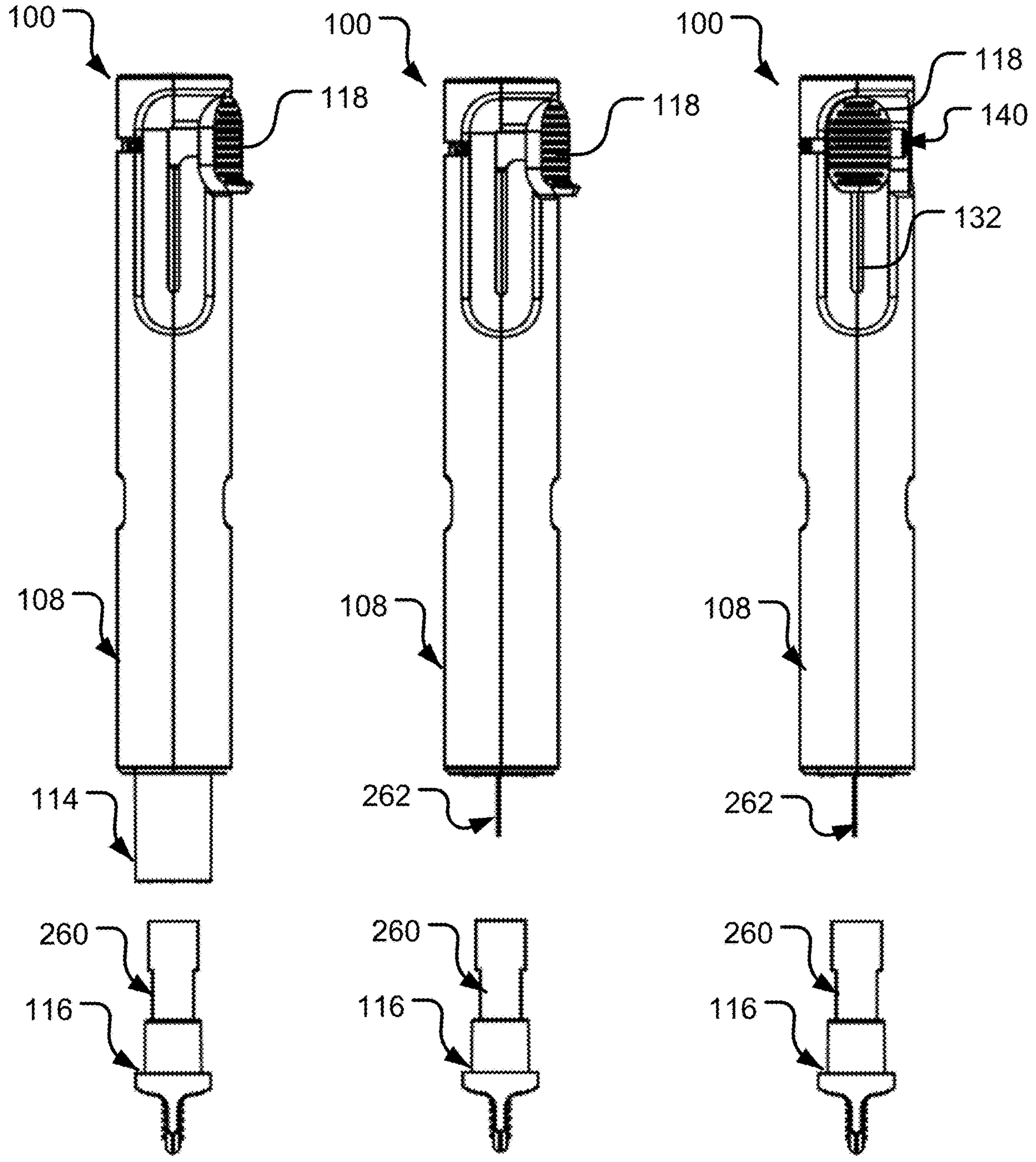
FIG. 11A is a side view of the injector with the injector cap and syringe cap coupled thereto removed from the distal tube.
FIG. 11B is a side view of the injector of FIG. 11A with the distal tube retracted.
FIG. 11C is a side view of the injector of FIG. 11B with the plunger slider rotated so it is distally depressible.

FIG. 11A through 11E depict the injector 100 in various stages of use. FIG. 11A is a side view of the injector 100 with the injector cap 116 and syringe cap 260 coupled thereto removed from the distal tube 114. In this view, the needle is shielded by the tube 114 of the injector 100, but the injector 100 is ready to be applied to the user.

FIG. 11B is a side view of the injector 100 of FIG. 11A with the distal tube 114 retracted. In this view, the user has applied the distal tube 114 to a portion of the body for injection. The applied force on the distal tube 114 is in the proximal direction (towards top of image) and is sufficient to overcome the biasing force of the biasing member 124 (not shown). Thus, as the distal tube 114 retracts into the casing 108, the needle 262 is exposed. It is noted that the needle 262 remains in a fixed position relative to the casing 108. That is, the needle 262 is exposed via retraction of the distal tube 114. And, the needle 262 is subsequently shielded by extension of the distal tube 114 over the needle 262. Referring back to FIG. 11B, in this view, the needle 262 would be inserted into the patient's skin.

FIG. 11C is a side view of the injector 100 of FIG. 11B with the plunger slider 118 rotated so it is distally depressible. With the needle 262 inserted into the skin, the user then rotates the plunger slider 118 transversely within the slider slot 140 so the stem (not shown) of the plunger slider is aligned with the longitudinal section 132 of the slider slot 140.

Figure 11D:
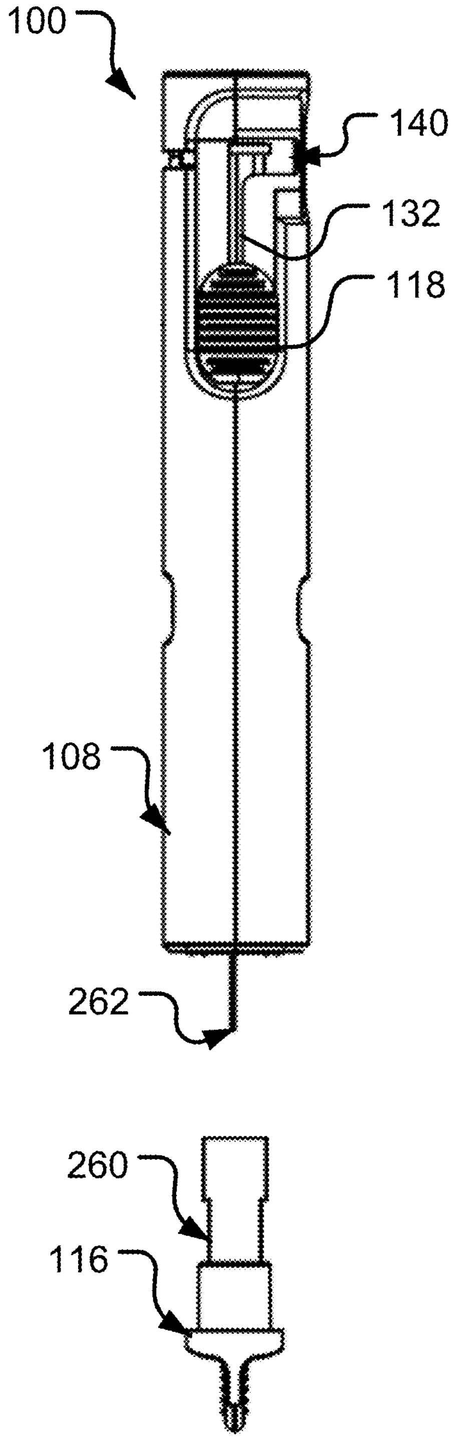
FIG. 11D is a side view of the injector of FIG. 11C with the plunger slider depressed distally.

FIG. 11D is a side view of the injector 100 of FIG. 11C with the plunger slider 118 depressed distally. Once the plunger slider 118 is aligned with the longitudinal section 132 of the slider slot 140, the plunger slider 118 is capable of being distally advanced so as to dispense the substance from the syringe. In this view, the user has dispensed the substance into the tissue.

Figure 11E:
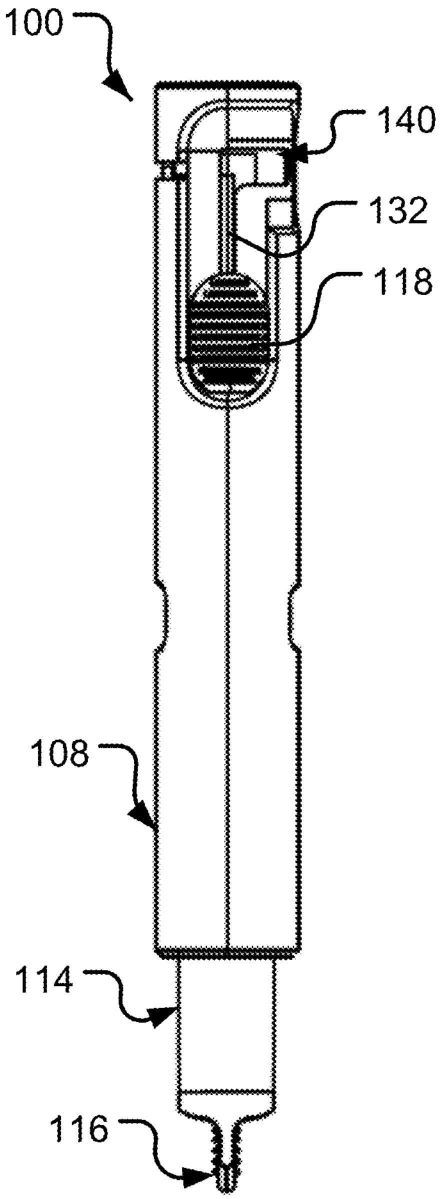
FIG. 11E is a side view of the injector of FIG. 11D with the injector cap and syringe cap coupled back to the distal tube and syringe, respectively.

FIG. 11E is a side view of the injector 100 of FIG. 11D with the injector cap 116 and syringe cap 260 coupled back to the distal tube 114 and syringe, respectively. After the plunger slider 118 is distally advanced, the user may proximally retract the injector 100 from the injection site. This causes the distal tube 114 to distally extend into the locked position. At this point, the syringe cap 260 and injector cap 116 may be reinserted in the distal tube 114. The image shows the syringe cap 260 being reinserted, but it may be sufficient to simply reinsert the injector cap 116.

Figure 12A:
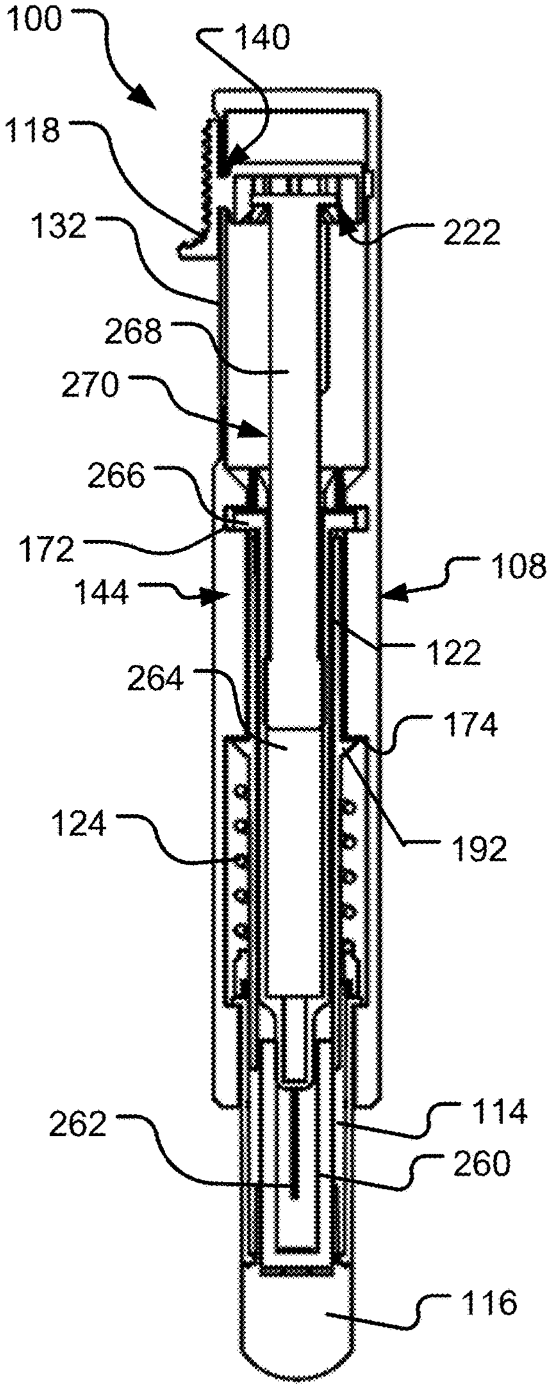
FIG. 12A is a cross-sectional side view of the injector prior to use and with the plunger slider rotated in order to view the internal components of the injector.

FIGS. 12A through 12F depict various images of the injector 100 in cross-section so the interaction of the various components is visible. These images depict the syringe 270 including the barrel 264 having a flange 266, the plunger 268, and the needle 262. FIG. 12A is a cross-sectional side view of the injector 100 prior to use and with the plunger slider 118 rotated so it is aligned with the longitudinal section 132 of the plunger slider slot 140 in order to view the internal components of the injector 100. As seen in the figure, the proximal end of the plunger 268 is positioned within the cavity 222 of the plunger slider 118. And, the flange 266 of the barrel 264 is positioned within the recesses 172 defined within the protrusions 144. Thus, the barrel 264 is restrained from distal and proximal movement within the casing 108, while the plunger 268 is distally moveable via the plunger slider 118. Also as seen in the figure, the barrel 264 of the syringe 270 is positioned within the cartridge 122 such that the flange 266 of the barrel 264 abuts the proximal end of the cartridge 122. The annular flange 192 abuts against the distally-facing surface 174 of the protrusions 144. In this way, the cartridge 122 is locked in place within the casing 108. As seen in the image, the syringe cap 260 is fitted within the injector cap 116 and is also fitted around the needle 262. Also, the syringe cap 260 and injector cap 116 are fitted to the distal tube 114 to shield the needle 262 prior to use. As seen in the image, the biasing member 124 is positioned around the cartridge 122 and is coupled between the cartridge 122 and the lock ring 126.

Figure 12B:
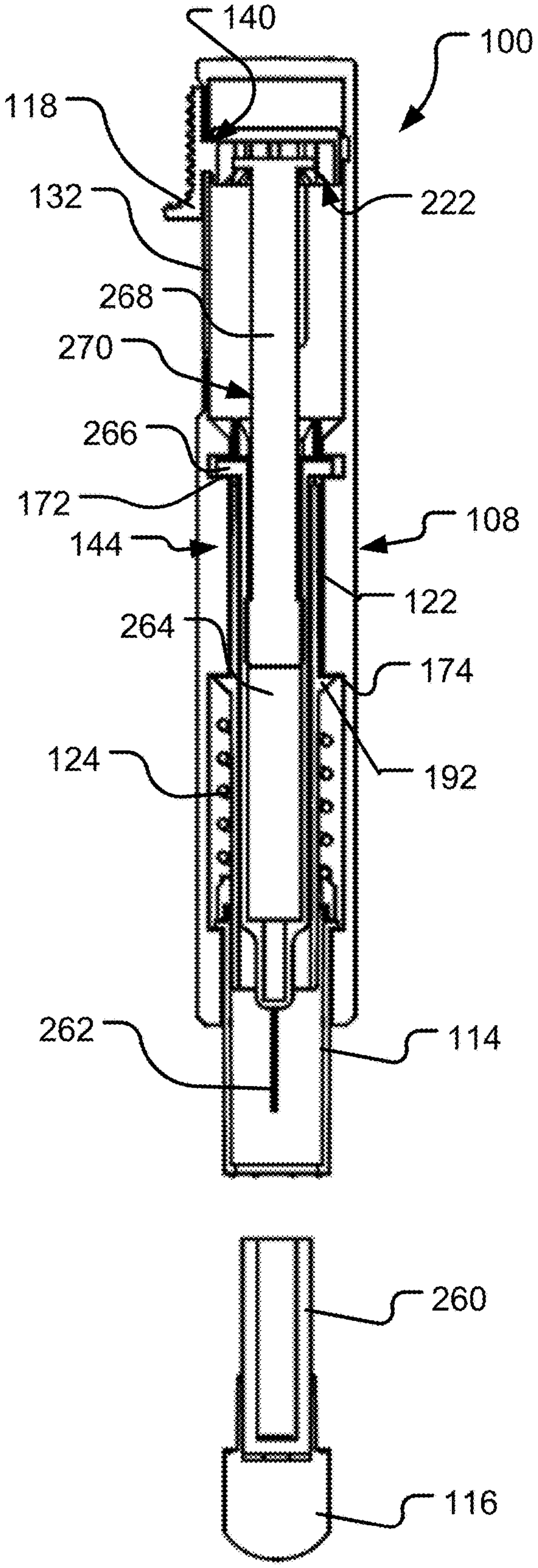
FIG. 12B is a cross-sectional side view of the injector of FIG. 12A with the injector cap and syringe cap (coupled thereto) removed from the distal tube.
Figure 12C:
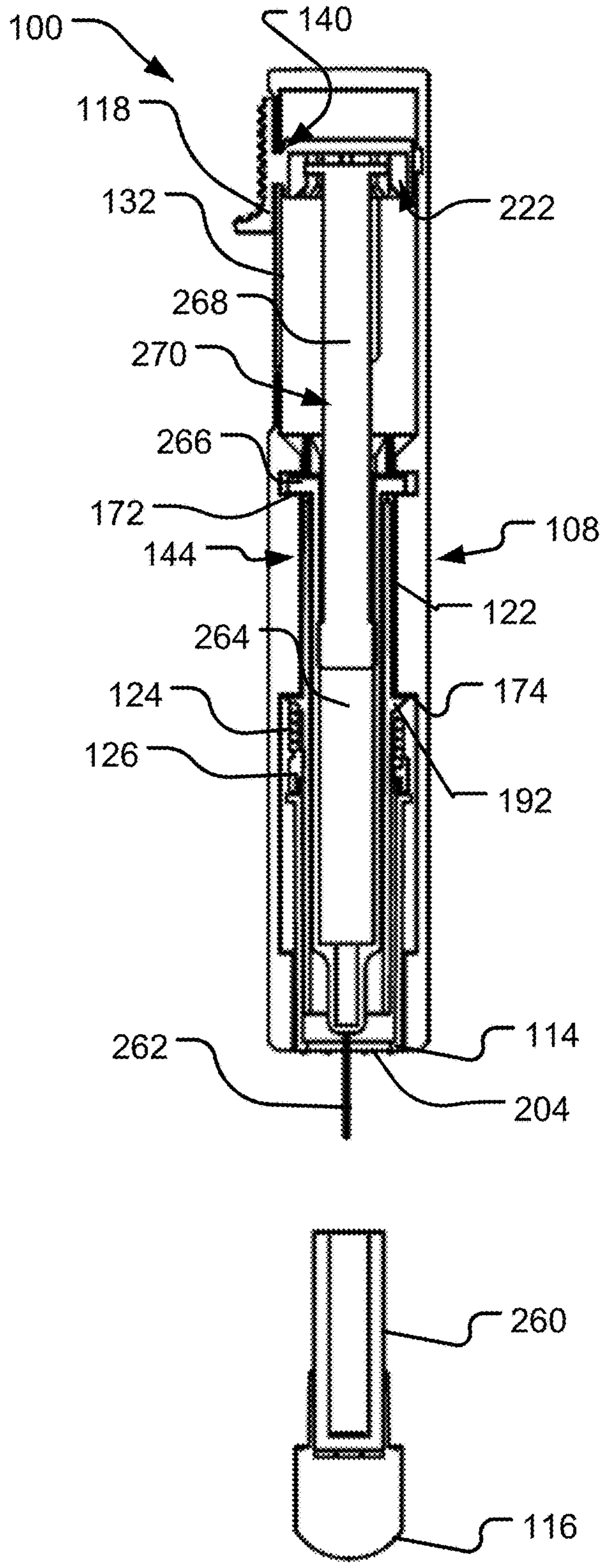
FIG. 12C is a cross-sectional side view of the injector of FIG. 12B with the distal tube retracted from, for example, application of the distal tube to a patient's skin.

FIG. 12B is a cross-sectional side view of the injector 100 of FIG. 12A with the injector cap 116 and syringe cap 260 (coupled thereto) removed from the distal tube 114. In this state, the needle 262 is shielded on the sides by the sidewall 206 of the distal tube 114. And since the distal tube 114 extends beyond the tip of the needle 262, the user is still shielded from accidental stick of the needle 262 prior to use. FIG. 12C is a cross-sectional side view of the injector 100 of FIG. 12B with the distal tube 114 retracted into the casing 108 as would occur during application of the distal tube 114 to the injection site of the user or patient. As seen in FIG. 12C, as the distal tube 114 retracts into the casing 108, the biasing member 124 is compressed between the lock ring 126 and the annular flange 192 of the cartridge 122. As described previously, the cartridge 122 is secured in place in the casing 108 and the syringe is secured within casing 108 (with the barrel 264 and needle 262 in a fixed position relative to the cartridge 122). As seen in FIG. 12C, the distal tube 114 is in a retracted position. In this position, the biasing member 124 is about fully compressed (no additional retraction is possible). In this state, the distal end 204 of the distal tube 114 is about flush with the distal end of the casing 108.

Figure 12D:
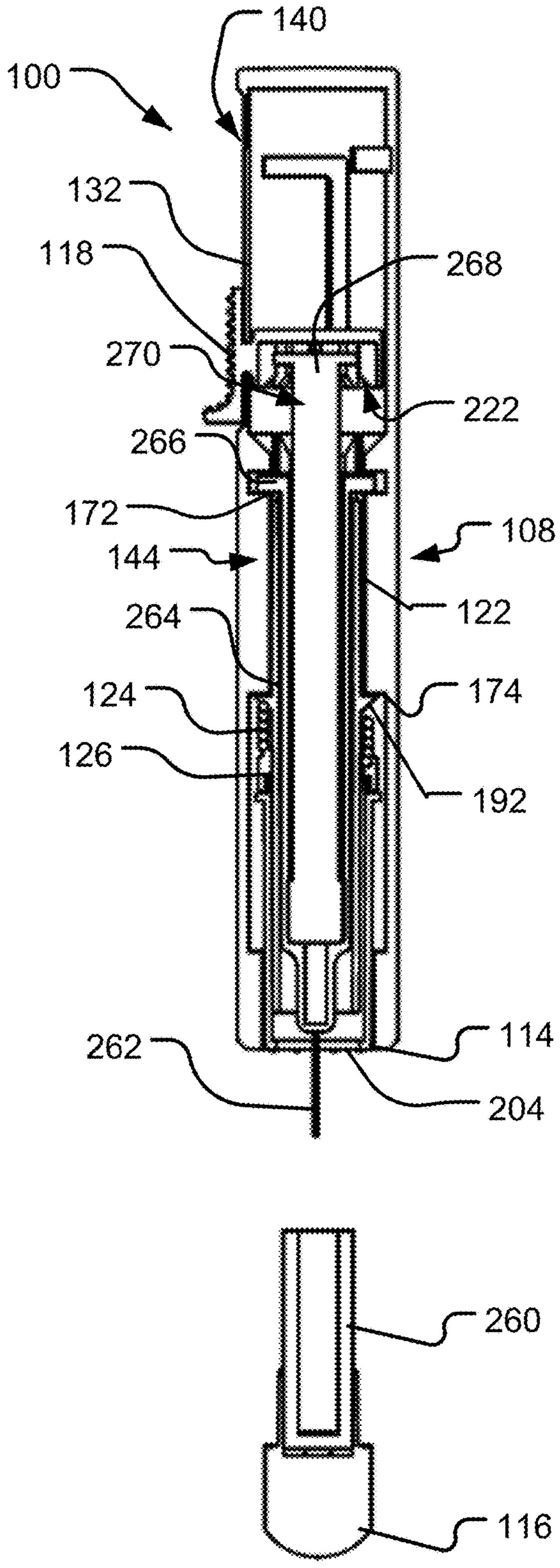
FIG. 12D is a cross-sectional side view of the injector of FIG. 12C with the plunger slider depressed distally so as to dispense the drug from the syringe.
Figure 12E:
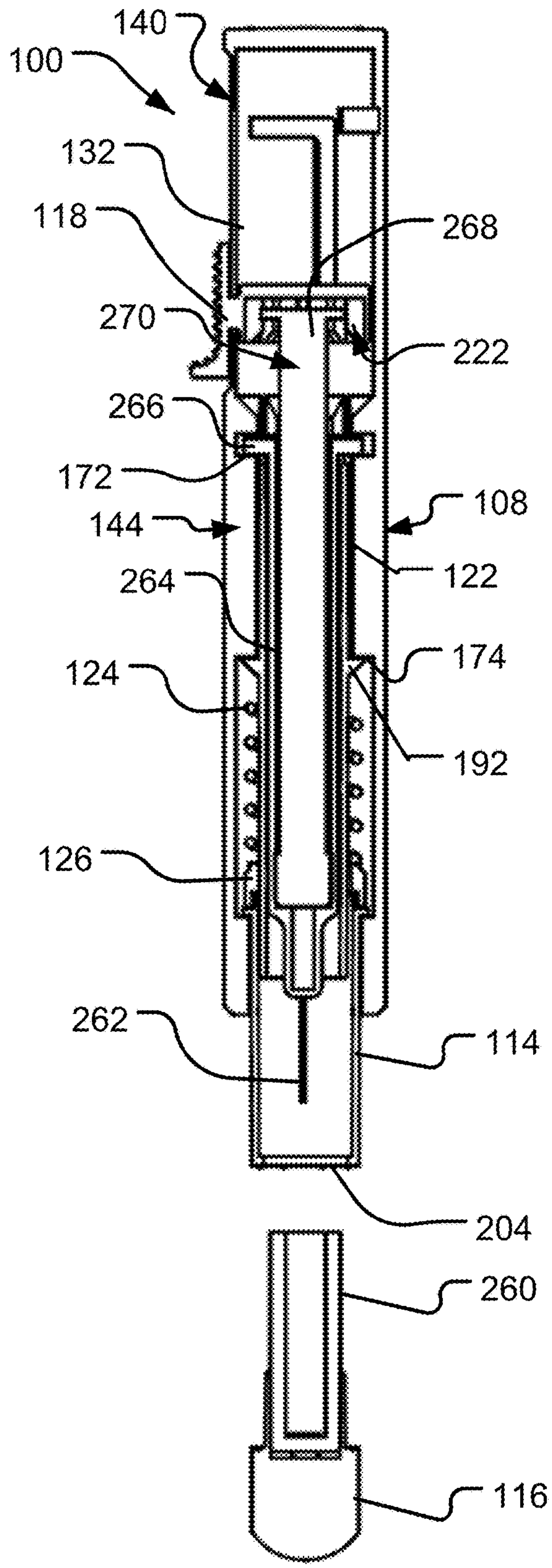
FIG. 12E is a cross-sectional side view of the injector of FIG. 12D with the distal tube advanced from, for example, the distal tube being removed from the patient's skin.
Figure 12F:
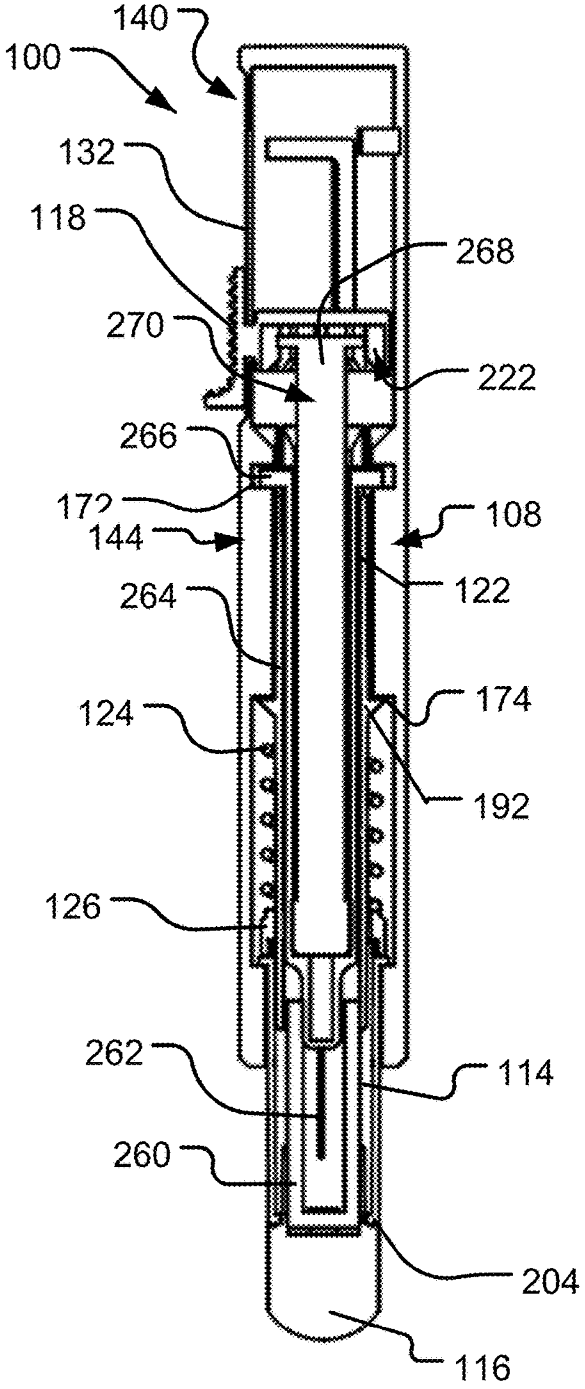
FIG. 12F is a cross-sectional side view of the injector of FIG. 12E with the injector cap and syringe cap returned to the distal tube.

FIG. 12D is a cross-sectional side view of the injector 100 of FIG. 12C with the plunger slider 118 depressed distally so as to dispense the substance from within the barrel 264 of the syringe 270. FIG. 12E is a cross-sectional side view of the injector 100 of FIG. 12D with the distal tube 114 extended into the locked and extended position. Finally, FIG. 12F is a cross-sectional side view of the injector 100 of FIG. 12E with the injector cap 116 and syringe cap 260 returned to the distal tube 114.

It is noted that as the user applies the distal tub 114 to the injection site, the needle 262 enters the injection site as the tube 114 transitions from the extended state to the retracted state. In the retracted state, the needle 262 is positioned within the patient at the injection site. After dispensing of the drug from the syringe, the user pulls the injector 100 away from the injection site, which causes the distal tube 114 to extend into an extended and locked position.

FIGS. 13A-13D illustrate how the injector 100 facilitates single-use operation. That is, the injector permits a single retraction of the distal tube 114 and then locking of the distal tube 114 in the extended position. Stated differently, the injector 100 is a single-use device that restricts exposing the needle 262 following the first use. It is noted that the syringe 270 has been dispensed in the images of FIGS. 13A and 13C. The purpose of the figures is to demonstrate the locking mechanism associated with distal tube 114, casing 108, lock ring 126, and biasing member 124. As such, the positioning of the plunger slider 118 and the plunger 268 are immaterial to this particular discussion.

Figure 13B:
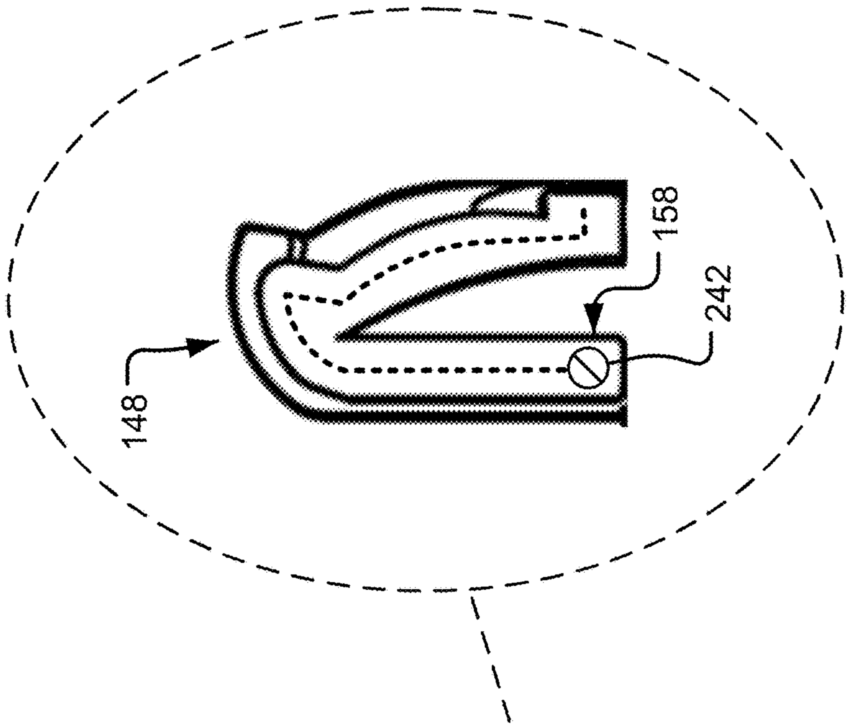
FIG. 13B is a close up and vertically flipped view of the track defined in the first casing with an image of the post of the lock ring positioned within the track. The post of the lock ring is positioned at the start of the track.
Figure 13A:
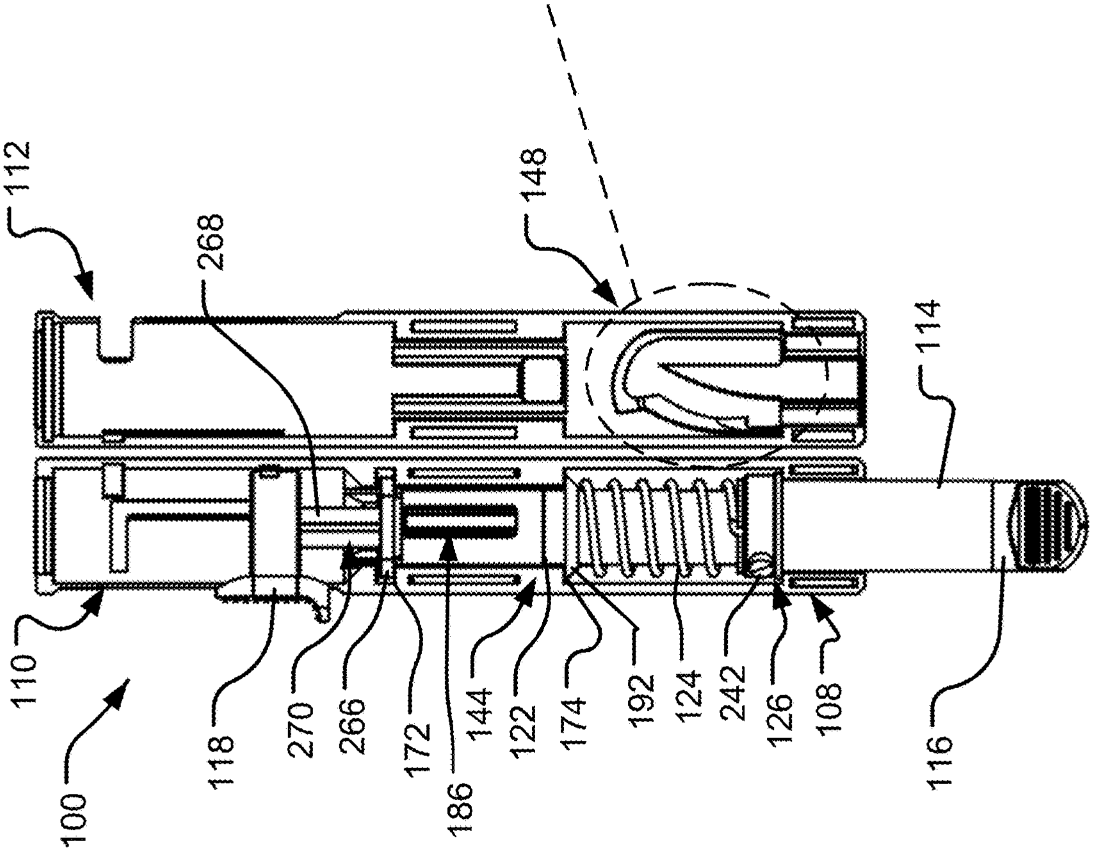
FIG. 13A is a side view of the injector with the first casings rotated away from the rest of the injector so as to expose the internal components thereof.

FIG. 13A is a side view of the injector 100 with the first casings 110 rotated away from the rest of the injector 100 so as to expose the internal components thereof. More particularly, the barrel 264 of the syringe 270 is positioned within the cartridge 122 and the flanges 266 are positioned within the recesses 172 of the casing 108. The cartridge 122 is secured within the casing 108 and is fixed in position via the annular flange 192 and the pair of projections 186. The biasing member 124 is coupled to the lock ring 126 and the annular flange 192 so as to bias the distal tube 114 in the extended position. The annular rim 210 of the distal tube 114 prevents further distal movement of the distal tube 114 relative to the casing 108. That is, the annular rim 210 prevent dislodgement of the distal tube 114 from the casing 108.

FIG. 13B is a close up and vertically flipped view of the track 148 defined in the first casing 110 with an image of the post 242 of the lock ring 126 positioned within the track 148. The image of FIG. 13B is flipped in order to simulate the movement of the post 242 relative to the track 148 when the first and second casings 110, 112 are coupled together. As seen in FIGS. 13A and 13B, the post 242 of the lock ring 126 is positioned at the start 158 of the track 148.

Figure 13D:
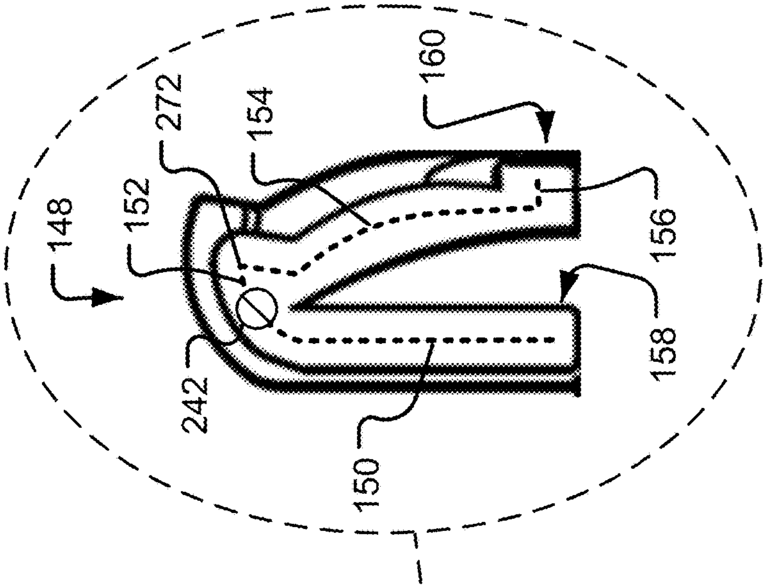
FIG. 13D is a close up and vertically flipped view of the track defined in the first casing with an image of the post of the lock ring positioned within the track. The post of the lock ring is positioned at about a midpoint between the start and locking end of the track.

When provided to the user with a pre-filled syringe 270 therein, the post 242 of the lock ring 126 is positioned at the start 158 of the track 148, as shown in FIGS. 13A and 13B. As the distal tube 114 is applied to the injection site of the patient, the distal tube 114 retracts into the casing 108. This causes the post 242 of the lock ring 126 to move proximally along the first longitudinal section 150 of the track 148. The post 242 proximally retracts and is guided along the transverse section 152 of the track 148, as seen in FIGS. 13C and 13D.

Figure 13C:
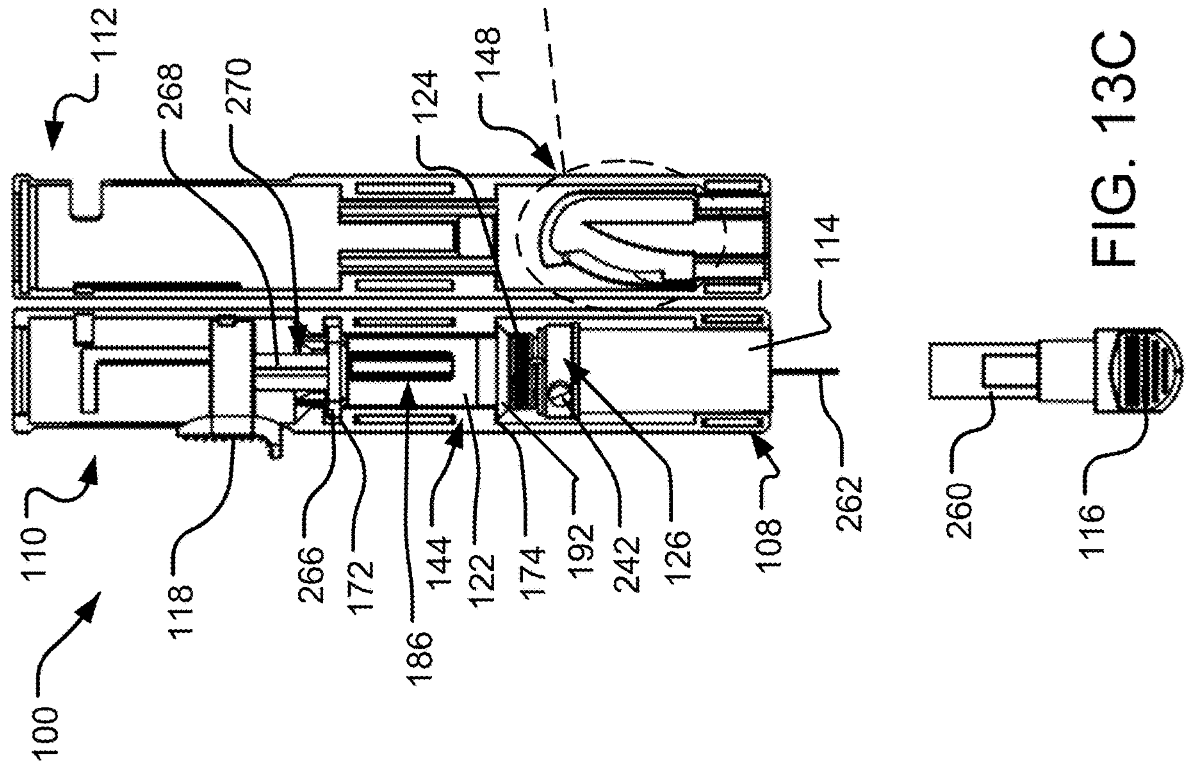
FIG. 13C is a side view of the injector with the first casings rotated away from the rest of the injector so as to expose the internal components thereof.

FIG. 13C is a side view of the injector 100 with the first casings 110 rotated away from the second casing 112 and the rest of the internal components of the injector 100. FIG. 13D is a close up and vertically flipped view of the track 148 defined in the first casing 110 with an image of the post 242 of the lock ring 126 positioned within the track 148. The post 242 of the lock ring 126 is positioned at the transverse section 152, which is about a midpoint between the start 158 and locking end 160 of the track 148. As described previously, when the post 242 enters the transverse section 152, the rotational bias of the biasing member 124 causes the lock ring 126 to rotate in the direction of the second longitudinal section 154. FIG. 13C shows the post 242 in the transition process through the transverse section 152.

In this position, the needle 262 is exposed and would be in the injection site of the patient. In this position, the user would dispense the drug from the syringe 270 by depressing the plunger slider 118, which is shown in FIG. 13C. At the most proximal retraction of the distal tube 114 relative to the casing 108, the post 242 would be positioned at the apex 272 of the track 148. In this position, when the user withdraws the injector 100 from the injection site, the distal tube 114 begins to extend. During this extension, the post 242 moves down along the second longitudinal section 154. If the distal tube 114 is permitted to fully extend, the post 242 encounters the end of the second longitudinal section 154, and the rotational bias of the biasing member 124 causes the post 242 to rotate into the transverse locking section 156 of the track 148. The biasing member 124 biases the post 242 into the end 160 of the track 148. The end 160 is defined by a trio of walls in which do not permit movement of the post 242. Therefore the distal tube 114 is locked in the extended position.

In this way, the injector 100 can be used to dispense a drug one time before it is locked. That is, the injector 100 is provided for use that permits a single injection by the needle and a subsequent locking of the injector 100.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

We claim:

1. An injector for use with a syringe having a plunger, a barrel, and a needle, the injector comprising:
- a cartridge configured to support the syringe;
- a casing including first and second openings, an inner surface, an outer surface opposite the inner surface, and a track defined on the inner surface, the casing configured to support the cartridge and the syringe;
- a tube including a tube distal end, the tube slidably engaged with the cartridge and configured to extend and retract relative to the first opening of the casing, wherein, in a retracted state of the tube and with the casing supporting the cartridge and the syringe, the needle of the syringe extends beyond the tube distal end and the first opening of the casing;
- a biasing member engaged with the cartridge and the tube so as to bias the tube in an extended state of the tube;
- a ring including a protrusion, the ring engaged with the tube and the biasing member, the protrusion positioned at least partially within the track; and
- a plunger slider configured to couple to the plunger of the syringe and comprising a portion that is positioned outside the casing when the plunger slider couples to the plunger of the syringe, wherein, when the plunger slider and the plunger of the syringe are coupled together, movement of the portion of the plunger slider and the plunger are fixed.

2. The injector of claim 1, wherein the cartridge and the casing are removably coupled together.

3. The injector of claim 1, wherein the plunger slider extends at least partially through the second opening.

4. The injector of claim 3, wherein the second opening extends through a sidewall of the casing.

5. The injector of claim 4, wherein the second opening includes a linear section.

6. The injector of claim 5, wherein the second opening includes a transverse section proximal to the linear section.

7. The injector of claim 1, wherein the inner surface defines an internal volume, and the plunger slider is configured to engage with the plunger of the syringe within the internal volume of the casing.

8. The injector of claim 1, wherein the protrusion of the ring is positioned at least partially within the track and is configured to lock the tube in the extended position after the tube has been in the retracted state.

9. The injector of claim 1, wherein the ring is configured to rotate relative to the tube at least partially when the ring is engaged with the tube and the biasing member.

10. The injector of claim 1, wherein the casing is configured to support the cartridge and the syringe in a fixed position relative to the casing during movement of the plunger slider.

11. The injector of claim 10, wherein the barrel of the syringe includes a flange, and the inner surface of the casing includes a structure configured to contact the flange of the barrel of the syringe to facilitate the fixed position of the syringe relative to the casing during movement of the plunger slider.

12. The injector of claim 1, wherein movement of the plunger slider is independent of movement of the tube.

13. The injector of claim 1, wherein rotation of the plunger slider is inhibited once the plunger slider is moved distally.

14. The injector of claim 1, further comprising the syringe.

15. The injector of claim 14, further comprising a medicament housed within the syringe.

16. The injector of claim 1, further comprising a cap configured to releasably couple to an end of the casing.

17. The injector of claim 1, wherein the inner surface defines an internal volume, and the plunger of the syringe is positioned entirely within the internal volume of the casing.

18. The injector of claim 1, wherein the plunger slider comprises a proximal-facing engagement surface for use in at least assisting to moving the plunger slider distally.

19. The injector of claim 18, wherein the plunger slider further comprises a side-facing engagement surface for use in at least assisting to moving the plunger slider distally.

20. The injector of claim 1, wherein a rate of movement of the plunger slider is manually controlled.

21. A method of employing the injector of claim 1 having the casing supporting the cartridge and the syringe, and wherein the syringe includes a medicament therein, the method comprises:

applying the tube to an injection site thereby causing the tube to be in the retracted state thereby causing the needle to enter the injection site;

depressing the plunger slider at a user-controlled rate thereby causing dispensing of at least some of the medicament from the syringe into the injection site; and removing the tube from the injection site thereby causing the tube to be locked in the extended state shielding the needle.

22. The method of claim 21, wherein depressing of the plunger slider is independent of applying the tube to the injection site.

23. The method of claim 21, wherein depressing the plunger slider is performed at a user-controlled amount to dispense all the medicament.

24. The method of claim 21, wherein depressing the plunger slider is performed at a user-controlled amount to dispense less than all the medicament.

* * * * *